United States Patent [19]

Aloup et al.

[11] Patent Number: 6,057,454
[45] Date of Patent: May 2, 2000

[54] 1-OXO-1H-INDEN-2-YL-1H-IMIDAZOLE-2-CARBOXYLIC ACID INTERMEDIATES

[75] Inventors: Jean-Claude Aloup, Villeneuve-le-Roi; François Audiau, Charenton-le-Pont; Michel Barreau, Montgeron; Dominique Damour, Orly; Arielle Genevois-Borella, Thiais; Jean-Claude Hardy, Cergy-Saint-Christophe; Patrick Jimonet, Villepreux; Franco Manfre, Limeil-Brevannes; Serge Mignani, Chatenay-Malabry; Patrick Nemecek, Thiais; Yves Ribeill, Villemoisson-sur-Orge, all of France

[73] Assignee: Rhone-Poulenc Rorer S.A., Antony, France

[21] Appl. No.: 09/205,689

[22] Filed: Dec. 4, 1998

Related U.S. Application Data

[62] Division of application No. 08/930,967, Oct. 3, 1997, Pat. No. 5,902,803.

[30] Foreign Application Priority Data

Apr. 5, 1995 [FR] France .................................. 95 04013

[51] Int. Cl.[7] ...................... C07D 233/90; C07D 401/10; C07D 413/10; C07D 403/10; C07F 9/6506
[52] U.S. Cl. .................. 548/334.5; 548/111; 548/314.7; 544/139; 546/210
[58] Field of Search ..................... 544/399, 139; 548/334.5, 111, 314.7; 546/199, 210; 540/603

[56] References Cited

FOREIGN PATENT DOCUMENTS 2 696 466   4/1994   France .

*Primary Examiner*—Mark L. Berch
*Assistant Examiner*—T. McKenzie
*Attorney, Agent, or Firm*—Finnegan, Henderson, Farabow, Garrett & Dunner, L.L.P.

[57] ABSTRACT

A compound of formula (II):

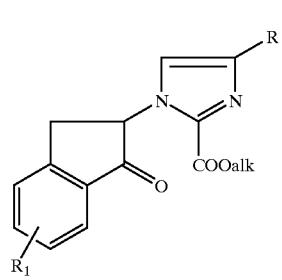

in which R is a hydrogen atom or a carboxy, alkoxycarbonyl, —CO—$NR_4R_5$, —$PO_3H_2$ or —$CH_2OH$ radical, and $R_1$ is an -alk-$NH_2$, -alk-NH—CO—$R_3$, -alk-$COOR_4$, -alk-CO—$NR_5R_6$ or —CO—NH—$R_7$ radical. The compounds of formula (II) can be used to prepare compounds of formula (I):

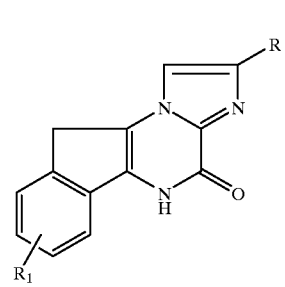

in which R and $R_1$ have the same meanings as above. The compounds of formula (I) have valuable pharmacological properties and are antagonists of the α-amino-3-hydroxy-5-methyl-4-isoxazolepropionic acid (AMPA) receptor, also known as the quisqualate receptor. The compounds of formula (I) are also non-competitive antagonists of the N-methyl-D-aspartate (NMDA) receptor and more specifically are ligands for NMDA receptor glycine modulator sites.

1 Claim, No Drawings

1-OXO-1H-INDEN-2-YL-1H-IMIDAZOLE-2-CARBOXYLIC ACID INTERMEDIATES

This is a division of application Ser. No. 08/930,967, filed Oct. 3, 1997 now U.S. Pat. No. 5,902,803, which is the national stage application of PCT/FR96/00496 filed on Apr. 2, 1996 which is incorporated herein by reference.

The present invention relates to compounds of formula:

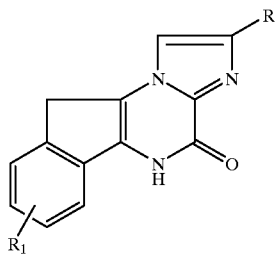

(I)

to their salts, to their enantiomers and diastereoisomers, to their preparation and to the medicaments containing them.

In the formula (I),

R represents a hydrogen atom or a carboxy, alkoxycarbonyl, —CO—NR$_4$R$_5$, —PO$_3$H$_2$ or —CH$_2$OH radical, R$_1$ represents an -alk-NH$_2$, -alk-NH—CO—R$_3$, -alk-COOR$_4$, -alk-CO—NR$_5$R$_6$ or —CO—NH—R$_7$ radical, R$_3$ represents an alkyl, phenyl, phenylalkyl, cycloalkyl or —NR$_6$R$_8$ radical, R$_4$ represents a hydrogen atom or an alkyl radical, R$_5$ represents a hydrogen atom or an alkyl, phenyl, cycloalkyl or phenylalkyl radical, R$_6$ represents a hydrogen atom or an alkyl radical, or else R$_5$ and R$_6$ form, with the nitrogen atom to which they are attached, a saturated or unsaturated, mono- or polycyclic heterocycle containing 1 to 6 carbon atoms and optionally one or a number of other heteroatoms chosen from O, S or N, R$_7$ represents a phenyl, phenylalkyl or -alk-COOR$_4$ radical, R$_8$ represents a hydrogen atom or an alkyl, cycloalkyl or phenylalkyl radical, alk represents an alkyl or alkylene radical.

Except where otherwise mentioned, in the preceding and following definitions, the alkoxy, alkyl and alkylene radicals and portions contain 1 to 6 carbon atoms and are in a straight or branched chain and the cycloalkyl radicals contain 3 to 6 carbon atoms.

Preferably, when R$_5$ and R$_6$ form a heterocycle with the nitrogen atom to which they are attached, this heterocycle is chosen from azetidine, pyrrolidine, piperidine, piperazine and morpholine rings.

The R$_1$ substituent is preferably in the 8- or 9-position.

The compounds of formula (I) can be prepared by the cyclization, in the presence of ammonium acetate, of a derivative of formula:

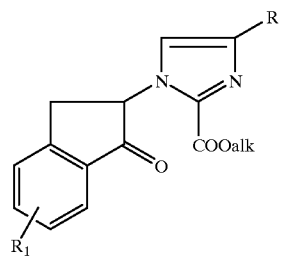

(II)

in which R and R$_1$ have the same meanings as in the formula (I) and alk represents an alkyl radical.

This cyclization is carried out in an organic acid, such as acetic acid, at the boiling temperature of the reaction mixture.

The derivatives of formula (II) are novel and form part of the invention. They can be obtained by reaction of an indanone of formula:

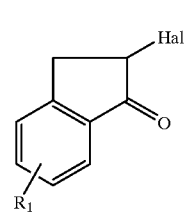

(III)

in which R$_1$ has the same meanings as in the formula (I), with a derivative of formula:

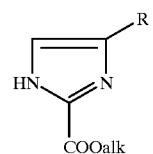

(IV)

in which R has the same meanings as in the formula (I) and alk represents an alkyl radical.

This reaction is generally carried out in an inert solvent, such as an alcohol (methanol or ethanol, for example), a ketone (acetone, for example), an aromatic hydrocarbon (toluene, for example) or dimethylformamide, or in the absence of solvent, optionally in the presence of a base, such as sodium hydride or potassium carbonate, with optionally a crown ether, such as 18C6, at a temperature of between 20° C. and the boiling temperature of the reaction mixture or the melting temperature of the reaction mixture.

The derivatives of formula (III) can be obtained by application or adaptation of the methods described by Olivier et al., Bull. Soc. Chim. France, 3092 (1973), in Patent DE 2,640,358 and in the examples.

The derivatives of formula (IV) can be obtained by application or adaptation of the methods described by P. S. Branco et al., Tetrahedron, 48 (30), 6335 (1992), J. E. Olivier et al., J. Org. Chem., 38 (7), 1437 (1973) and in U.S. Pat. No. 3,600,399 and in the examples.

The compounds of formula (I) in which R represents a carboxy radical and/or R$_1$ represents an -alk-COOR$_4$ radical in which R$_4$ represents a hydrogen atom or a —CO—NH—R$_7$ radical in which R$_7$ represents an -alk-COOR$_4$ radical and $R_4$ represents a hydrogen atom can also be prepared by hydrolysis of a corresponding compound of formula (I) in which R represents an alkoxycarbonyl radical and/or $R_1$ represents an -alk-COOR$_4$ radical in which $R_4$ represents an alkyl radical or a —CO—NH—R$_7$ radical in which $R_7$ represents an -alk-COOR$_4$ radical and $R_4$ represents an alkyl radical.

This reaction is generally carried out by means of a base, such as an alkali metal hydroxide (sodium hydroxide or potassium hydroxide, for example), in a mixture of an inert solvent (dioxane, for example) and water, at a temperature of between 20° C. and the boiling temperature of the reaction mixture, or by means of an inorganic acid, such as hydrochloric acid, in an inert solvent, such as dioxane and acetic acid, at the boiling temperature of the reaction mixture.

The compounds of formula (I) in which R represents a —PO$_3$H$_2$ radical can also be prepared by hydrolysis of a derivative of formula:

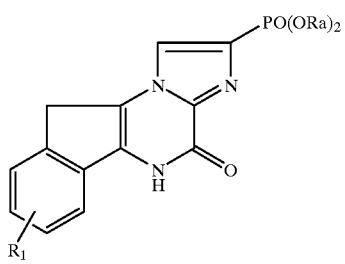

(V)

in which $R_1$ has the same meanings as in the formula (I) and Ra represents a methyl, ethyl or benzyl radical.

This reaction is generally carried out by means of bromotrimethylsilane, in a chlorinated solvent (dichloromethane or chloroform, for example), at a temperature in the region of 20° C. The derivatives (V) can be obtained by a cyclization analogous to that described above for obtaining the compounds of formula (I) and from the method described in the examples.

The compounds of formula (I) in which R represents a —CH$_2$OH radical can also be prepared by reduction of a corresponding compound of formula (I) in which R represents an alkoxycarbonyl radical.

This reduction is generally carried out by means of a hydride of lithium and boron or of lithium and aluminium, in an inert solvent, such as tetrahydrofuran or dioxane, at a temperature of between 20° C. and the boiling temperature of the reaction mixture.

The compounds of formula (I) in which R represents a —CO—NR$_4$R$_5$ radical can also be prepared by reaction of an aluminium complex, formed from a trialkylaluminium (trimethylaluminium, for example) and the hydrochloride of an amine HNR$_4$R$_5$, with a corresponding compound of formula (I) in which R represents an alkoxycarbonyl radical.

This reaction is generally carried out in an inert solvent, such as a hydrocarbon (toluene, for example), at a temperature of between 20° C. and the boiling temperature of the reaction mixture.

The amines HNR$_4$R$_5$ are commercially available or can be obtained by reaction of the primary amine H$_2$NR$_5$ with a derivative HalR$_4$ in which Hal represents a halogen atom (chlorine or bromine, for example) and $R_4$ has the same meanings as in the formula (I), with the exception of hydrogen. This reaction is generally carried out in an inert solvent, such as dimethylformamide, in the presence of a trialkylamine (triethylamine, for example), at a temperature in the region of 20° C.

The compounds of formula (I) in which $R_1$ represents an -alk-NH—CO—R$_3$ radical in which $R_3$ represents a (1C) alkyl radical can also be prepared by reaction of a corresponding compound of formula (I), in which $R_1$ represents an -alk-NH$_2$ radical, with acetic anhydride.

This reaction is generally carried out without solvent or in an inert solvent, such as acetic acid or dimethylformamide, at a temperature in the region of 20° C., optionally in the presence of a base, such as a trialkylamine (triethylamine, for example) or sodium acetate.

The compounds of formula (I) in which $R_1$ represents an -alk-NH—CO—R$_3$ radical in which $R_3$ represents an —NR$_6$R$_8$ radical, $R_6$ represents a hydrogen atom and $R_8$ represents a hydrogen atom or an alkyl, cycloalkyl or phenylalkyl radical can also be prepared by reaction of a corresponding compound of formula (I), in which $R_1$ represents an -alk-NH$_2$ radical, with an isocyanate $R_b$—NCO in which $R_b$ represents a trimethylsilyl, alkyl, cycloalkyl or phenylalkyl radical, optionally followed by hydrolysis of the silylated derivative.

This reaction is generally carried out in an inert solvent, such as dimethylformamide, tetrahydrofuran or dioxane, at a temperature of between 20° C. and the boiling temperature of the reaction mixture. Hydrolysis of the silylated derivative is carried out at a temperature of between 20 and 50° C.

The compounds of formula (I) in which $R_1$ represents an -alk-NH—CO—R$_3$ radical in which $R_3$ represents an —NR$_6$R$_8$ radical, $R_6$ represents a hydrogen atom and $R_8$ represents an alkyl, cycloalkyl or phenylalkyl radical can also be prepared by reaction of a corresponding compound of formula (I), in which $R_1$ represents an -alk-NH$_2$ radical, with a derivative of formula:

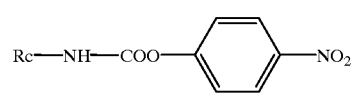

(VI)

in which Rc represents an alkyl, cycloalkyl or phenylalkyl radical.

This reaction is generally carried out in an inert solvent, such as dimethylformamide, tetrahydrofuran or dioxane, at a temperature of between 20° C. and the boiling temperature of the reaction mixture.

The derivatives of formula (VI) can be obtained by application or adaptation of the methods described by J. Izdebski et al., Synthesis, 423 (1989) and T. Konakahara et al., Synthesis, 103 (1993).

The compounds of formula (I) in-which $R_1$ represents an -alk-NH—CO—R$_3$ radical in which $R_3$ represents an alkyl, phenyl, phenylalkyl, cycloalkyl or —NR$_6$R$_8$ radical, $R_6$ represents an alkyl radical and $R_8$ represents an alkyl, cycloalkyl or phenylalkyl radical can also be prepared by reaction of a corresponding compound of formula (I), in which $R_1$ represents an -alk-NH$_2$ radical, with a Hal-CO—R$_3$ derivative in which Hal represents a halogen atom, and preferably a chlorine atom, and $R_3$ has the same meanings as above.

This reaction is preferably carried out in an inert solvent, such as dimethylformamide, in the presence of an acid acceptor, such as a trialkylamine (triethylamine, for example), at a temperature of between 20° C. and the boiling temperature of the reaction mixture.

The Hal-CO—R$_3$ derivatives are commercially available or those in which $R_3$ represents an —NR$_6$R$_8$ radical can be prepared by reaction of the amine HNR$_6$R$_8$ with phosgene by application or adaptation of the method described by H. Tilles, J. Am. Chem. Soc., 81, 714 (1959). The amines HNR$_6$R$_8$ are commercially available or can be obtained by reaction of the primary amine H$_2$NR$_8$ with a derivative HalR$_6$ in which Hal represents a halogen atom (chlorine or bromine, for example) and R$_6$ has the same meanings as in the formula (I), with the exception of hydrogen. This reaction is generally carried out in an inert solvent, such as dimethylformamide, in the presence of a trialkylamine (triethylamine, for example), at a temperature in the region of 20° C.

The compounds of formula (I) in which R$_1$ represents an -alk-CO—NR$_5$—R$_6$ radical can also be prepared by reaction of a corresponding compound of formula (I), in which R$_1$ represents an -alk-COOR$_4$ radical or, when R$_4$ represents a hydrogen atom, a reactive derivative of this acid, with an amine HNR$_5$R$_6$.

When the acid is used, the reaction is carried out in the presence of a coupling agent used in peptide chemistry, such as a carbodiimide (for example, N,N'-dicyclohexylcarbodiimide or 1-(3-dimethylaminopropyl)-3-ethylcarbodiimide) or N,N'-diimidazole carbonyl, in an inert solvent, such as an ether (tetrahydrofuran or dioxane, for example), an amide (dimethylformamide) or a chlorinated solvent (methylene chloride, 1,2-dichloroethane or chloroform, for example), optionally in the presence of hydroxybenzotriazole, at a temperature of between 0° C. and the reflux temperature of the reaction mixture. When an ester is used, the reaction is then carried out either in an organic medium, optionally in the presence of an acid acceptor, such as a nitrogenous organic base (trialkylamine, pyridine, 1,8-diazabicyclo[5.4.0]undec-7-ene or 1,5-diazabicyclo[4.3.0] non-5-ene, for example), in a solvent such as mentioned above or a mixture of these solvents or a lower aliphatic alcohol, at a temperature of between 0° C. and the reflux temperature of the reaction mixture, or in a two-phase aqueous/organic medium in the presence of an alkali metal or alkaline-earth metal base (sodium hydroxide or potassium hydroxide) or of an alkali metal or alkaline-earth metal carbonate or bicarbonate at a temperature of between 0 and 40° C.

The amines HNR$_5$R$_6$ are commercially available or can be obtained by reaction of the primary amine H$_2$NR$_5$ with a derivative HalR$_6$ in which Hal represents a halogen atom (chlorine or bromine, for example) and R$_6$ has the same meanings as in the formula (I), with the exception of hydrogen. This reaction is generally carried out in an inert solvent, such as dimethylformamide, in the presence of a trialkylamine (triethylamine, for example), at a temperature in the region of 20° C.

The compounds of formula (I) in which R$_1$ represents a -(1C)alk-NH$_2$ radical can also be prepared by hydrogenation of a derivative of formula:

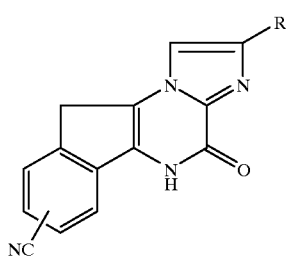

(VII)

in which R has the same meanings as in the formula (I).

This hydrogenation is generally carried out by means of hydrogen, in an inert solvent, such as acetic acid, trifluoroacetic acid or a mixture of these solvents, in the presence of a hydrogenation catalyst, such as palladium-on-charcoal, under pressure (approximately 50 bar), at a temperature in the region of 20° C.

The derivatives of formula (VII) can be obtained by cyclization of a derivative of formula:

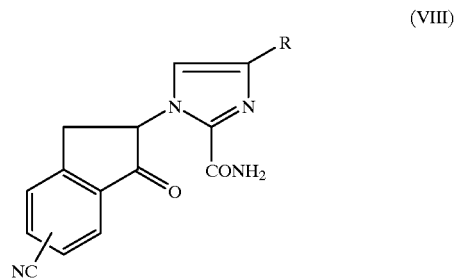

(VIII)

in which R has the same meanings as in the formula (I).

This cyclization is generally carried out in acetic acid, at the boiling temperature of the reaction mixture.

The derivatives of formula (VIII) can be obtained by reaction of ammonia with the ester of formula:

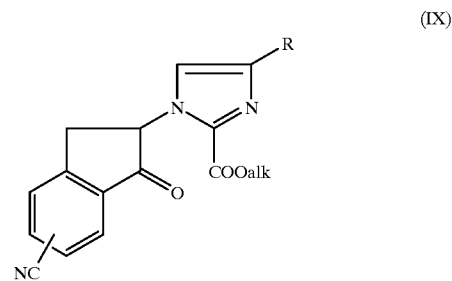

(IX)

in which R has the same meanings as in the formula (I) and alk represents an alkyl radical.

This reaction is generally carried out in an inert solvent, such as a lower aliphatic alcohol (methanol or ethanol, for example), at a temperature in the region of 20° C.

The derivatives of formula (IX) can be obtained by application or adaptation of the method described in the examples.

It is understood by the person skilled in the art that, for the implementation of the processes according to the invention described above, it may be necessary to introduce protecting groups for the amino, carboxy and alcohol functional groups in order to prevent side reactions. These groups are those which are capable of being removed without affecting the remainder of the molecule. Mention may be made, as examples of protecting groups for the amino functional group, of tert-butyl or methyl carbamates which can be regenerated by means of iodotrimethylsilane or phthalimido derivatives which-can be regenerated by means of hydrazine or of methylhydrazine or in acid medium (hydrobromic acid, for example). Mention may be made, as protecting groups for carboxy functional groups, of esters (methoxymethyl ester, tetrahydropyranyl ester, benzyl ester or tert-butyl ester, for example), oxazoles and 2-alkyl-1,3-oxazolines. Mention may be made, as protecting groups for alcohol functional groups, of esters (benzoyl ester, for example) or ethers (methoxyethoxymethyl, tityl or tetrahydropyrranyl), which can be regenerated in acid medium. Other protecting groups which can be used are described by W. Greene et al., Protecting Groups in Organic Synthesis, second edition, 1991, John Wiley & Sons.

The compounds of formula (I) can be purified by the usual known methods, for example by crystallization, chromatography or extraction.

The enantiomers of the compounds of formula (I) can be obtained by resolution of the racemates, for example by chromatography on a chiral column, according to W. H. Pirckle et al., Asymmetric Synthesis, vol. 1, Academic Press (1983), or by synthesis from chiral precursors.

The diastereoisomers of the compounds of formula (I) can be separated by the usual known methods, for example by crystallization or chromatography.

The compounds of formula (I) containing a basic residue can optionally be converted to addition salts with an inorganic or organic acid by the action of such an acid in an organic solvent such as an alcohol, a ketone, an ether or a chlorinated solvent.

The compounds of formula (I) containing an acid residue can optionally be converted to metal salts or to addition salts with nitrogenous bases according to methods known per se. These salts can be obtained by the action of a metal base (alkali metal or alkaline-earth metal base, for example), ammonia, an amine or a salt of an amine on a compound of formula (I), in a solvent. The salt formed is separated by the usual methods.

These salts also form part of the invention.

There may be mentioned, as examples of pharmaceutically acceptable salts, the addition salts with inorganic or organic acids (such as acetate, propionate, succinate, benzoate, fumarate, maleate, oxalate, methanesulphonate, isethionate, theophyllinacetate, salicylate, methylenebis(β-hydroxynaphthoate), hydrochloride, sulphate, nitrate and phosphate), the salts with alkali metals (sodium, potassium or lithium) or with alkaline-earth metals (calcium or magnesium), the ammonium salt or the salts of nitrogenous bases (ethanolamine, trimethylamine, methylamine, benzylamine, N-benzyl-β-phenethylamine, choline, arginine, leucine, lysine or N-methylglucamine).

The compounds of formula (I) exhibit advantageous pharmacological properties. These compounds are antagonists of the α-amino-3-hydroxy-5-methyl-4-isoxazolepropionic acid (AMPA) receptor, also known under the name of the quisqualate receptor.

Moreover, the compounds of formula (I) are noncompetitive antagonists of the N-methyl-D-aspartate (NMDA) receptor and, more particularly, they are ligands for the glycine-modulatory sites of the NMDA receptor.

These compounds are thus useful for treating or preventing all ischaemias (such as focal or global ischaemia) resulting from cerebrovascular accidents such as thromboembolic and haemorrhagic stroke, a cardiac arrest, arterial hypotension, a heart, vascular or pulmonary surgical operation or severe hypoglycaemia. They are also useful in the treatment of effects due to anoxia, whether perinatal or resulting from drowning, high pressure or cerebrospinal lesions. These compounds can also be used for treating or preventing the development of neurodegenerative diseases, Huntington's chorea, Alzheimer's disease and other dementias, amyotrophic lateral sclerosis or other motoneuron diseases, olivopontocerebellar atrophy and Parkinson's disease. These compounds can also be used with respect to epileptogenic and/or convulsive symptoms, for the treatment of cerebral or spinal traumas, of traumas related to degeneration of the inner ear (R. Pujol et al., Neuroreport, 3, 299–302 (1992)) or of the retina (J. L. Monsinger et al., Exp. Neurol., 113, 10–17 (1991)), of tinnitus, of anxiety (Kehne et al., Eur. J. Pharmacol., 193, 283 (1991)), of depression (Trullas et al., Eur. J. Pharmacol., 185, 1 (1990)), of schizophrenia (Reynolds, TIPS, 13, 116 (1992)), of Tourette's syndrome, of hepatic encephalopathies, of sleep disorders, of attention deficit disorders or of disorders of hormonal conditions (excess secretion of HG or HL or secretion of corticosterone), as analgesics (Dickenson et al., Neurosc. Letters, 121, 263 (1991)), antiinflammatories (Sluta et al., Neurosci. Letters, 149, 99–102 (1993)), antianorexics (Sorrels et al., Brain Res., 572, 265 (1992)), antimigraines and antiemetics, and for treating poisonings by neurotoxins or other agonist substances of the NMDA or AMPA receptor, and neurological disorders associated with viral diseases such as viral meningitides and encephalitides, AIDS (Lipton et al., Neuron, 7, 111 (1991)), rabies, measles and tetanus (Bagetta et al., Br. J. Pharmacol., 101, 776 (1990)). These compounds are also useful for preventing, tolerating and depending on symptoms of withdrawal from drugs or from alcohol and inhibiting addiction to and dependence on opiates, barbiturates, amphetamine and benzodiazepines. They can also be used in the treatment of deficiencies related to mitochondrial anomalies such as mitochondrial myopathy, Leber's syndrome, Wernicke's encephalopathy, Rett's syndrome, homocysteinaemia, hyperprolinaemia, hydroxybutiricaminoaciduria, saturnine encephalopathy (chronic lead poisoning) and sulphite oxidase deficiency.

The affinity of the compounds of formula (I) with respect to the AMPA receptor was determined by studying the antagonism of the specific binding of [$^3$H]-AMPA on rat cerebral cortex membranes (Honoré et al., Neuroscience Letters, 54, 27 (1985)). The [$^3$H]-AMPA is incubated in the presence of 0.2 mg of proteins at 4° C. for 30 minutes in 10 mM $KH_2PO_4$, 100 mM KSCN, pH 7.5 buffer. The non-specific binding is determined in the presence of 1 mM L-glutamate. The bonded radioactivity is separated by filtration on Pharmacia filters (Printed Filtermate A). The inhibiting activity of these products is less than or equal to 100 µM.

The affinity of the compounds of formula (I) for the glycine site linked to the NMDA receptor was determined by studying the antagonism of the specific binding of [$^3$H]-DCKA on rat cerebral cortex membranes according to the method described by T. Canton et al., J. Pharm. Pharmacol., 44, 812 (1992). The [$^3$H]-DCKA (20 nM) is incubated in the presence of 0.1 mg of proteins at 4° C. for 30 minutes in 50 mM, pH 7.5, HEPES buffer. The non-specific binding is determined in the presence of 1 mM glycine. The bonded radioactivity is separated by filtration on Whatman GF/B filters. The inhibiting activity of these products is less than or equal to 100 µM.

The compounds of formula (I) have a low toxicity. Their $LD_{50}$ in mice is greater than 50 mg/kg by the IP route.

The preferred compounds of formula (I) are those in which R represents a hydrogen atom or a carboxy radical, $R_1$ represents an -alk-NH—CO—$R_3$, -alk-COOR$_4$, -alk-CO—NR$_5$R$_6$ or —CO—NH—R$_7$ radical, $R_3$ represents an alkyl or —NR$_6$R$_8$ radical, $R_4$ represents a hydrogen atom, $R_5$ represents a hydrogen atom, $R_6$ represents an alkyl radical and $R_7$ represents a phenylalkyl or -alk-COOR$_4$ radical.

Among the latter are preferred the following compounds:
(4,5-dihydro-4-oxo-10H-imidazo[1,2-a]indeno[1,2-e]pyrazin-9-yl)acetic acid,
N-methyl-2-(4,5-dihydro-4-oxo-10H-imidazo[1,2-a]indeno[1,2-e]pyrazin-9-yl)acetamide,
N-[(4,5-dihydro-4-oxo-10H-imidazo[1,2-a]indeno[1,2-e]pyrazin-9-yl)methyl]acetamide, 9-[(3-methylureido)methyl]-5H,10H-imidazo[1,2-a]indeno [1,2-e]pyrazin-4-one,
N-methyl-[4,5-dihydro-4-oxo-10H-imidazo[1,2-a]indeno[1, 2-e]pyrazin-8-yl]acetamide,
8-N-methylcarboxamidomethyl-4,5-dihydro-4-oxo-10H- imidazo[1,2-a]indeno[1,2-e]pyrazin-2-carboxylic acid,
8-carboxymethyl-4,5-dihydro-4-oxo-10H-imidazo[1,2-a] indeno[1,2-e]pyrazin-2-carboxylic acid,
8-(3-methylureido)methyl-5H,10H-imidazo[1,2-a]indeno [1,2-e]pyrazin-4-one,
9-carboxymethyl-4,5-dihydro-4-oxo-10H-imidazo[1,2-a] indeno[1,2-e]pyrazin-2-carboxylic acid,
N-benzyl-(4,5-dihydro-4-oxo-10H-imidazo[1,2-a]indeno[1, 2-e]pyrazin-9-yl)carboxamide,
N-[(4,5-dihydro-4-oxo-10H-imidazo[1,2-a]indeno[1,2-e] pyrazin-9-yl) carbonyl]glycine,
N-benzyl-(4,5-dihydro-4-oxo-10H-imidazo[1,2-a]indeno[1, 2-e]pyrazin-8-yl)carboxamide,
8-(N-ethylaminocarbonylmethyl)-4,5-dihydro-4-oxo-10H- imidazo[1,2-a]indeno[1,2-e]pyrazin-2-carboxylic acid,
ethyl 8-(N-ethylaminocarbonylmethyl)-4,5-dihydro-4-oxo- 10H-imidazo[1,2-a]indeno[1,2-e]pyrazin-2-carboxylate,
9-N-benzylcarbamoyl-4,5-dihydro-4-oxo-10H-imidazo[1,2- a]indeno[1,2-e]pyrazin-2-carboxylic acid,
8-(2-carboxyethyl)-4,5-dihydro-4-oxo-10H-imidazo[1,2-a] indeno[1,2-e]pyrazine-2-carboxylic acid,
9-[(3-methylureido)methyl]-4,5-dihydro-4-oxo-10H- imidazo[1,2-a]indeno[1,2-e]pyrazin-2-carboxylic acid,
9-carboxymethyl-4,5-dihydro-4-oxo-10H-imidazo[1,2-a] indeno[1,2-e]pyrazin-2-phosphonic acid,
9-N-methylaminocarbonylmethyl-4,5-dihydro-4-oxo-10H- imidazo[1,2-a]indeno[1,2-e]pyrazin-2-carboxylic acid,
9-(1-carboxyethyl)-4,5-dihydro-4-oxo-10H-imidazo[1,2-a] indeno[1,2-e]pyrazin-2-carboxylic acid, their salts and their enantiomers and diastereoisomers.

The following examples illustrate the invention.

EXAMPLE 1

37.5 ml of 8N hydrochloric acid are added to a suspension, under an argon atmosphere, of 3.09 g of the ethyl ester of (4,5-dihydro-4-oxo-10H-imidazo[1,2-a] indeno[1,2-e]pyrazin-9-yl)acetic acid in 150 ml of dioxane, which suspension is heated to 40° C., and the mixture is then heated for 90 hours. The reaction mixture is concentrated to dryness under reduced pressure (15 mm Hg, 2 kPa) at 40° C. The evaporation residue is taken up in 200 ml of distilled water, stirred, filtered, washed with water and then twice with 40 ml of isopropyl ether and dried under reduced pressure (1 mm Hg; 0.13 kPa). The product thus obtained (3.8 g) is dissolved in 125 ml of 0.1N sodium hydroxide solution by passing through ultrasound. The organic phase is extracted with 25 ml of ethyl acetate. The aqueous phase is treated with 0.3 g of vegetable charcoal, filtered and acidified with 1.3 ml of 1N hydrochloric acid. The precipitate formed is filtered, washed with water and dried under reduced pressure (1 mm Hg; 0.13 kPa) at 60° C. The product is dissolved in 40 ml of 0.1N sodium hydroxide solution and the aqueous phase is filtered, then diluted with 60 ml of distilled water and lyophilized. 1.2 g of the sodium salt of (4,5-dihydro-4-oxo-10H-imidazo[1,2-a]indeno[1,2-e] pyrazin-9-yl)acetic acid are thus obtained in the form of a light-beige lyophilisate, the melting point of which is greater than 260° C. (Analysis C15H10N3NaO3; % Calculated C: 59.41, H: 3.32, N: 13.86; % Found C: 59.6, H: 3.4, N: 13.50).

EXAMPLE 2

10.15 g of the ethyl ester of 1-(4-ethoxycarbonylmethyl- 1-oxoindan-2-yl)imidazole-2-carboxylic acid and 22 g of ammonium acetate are heated at reflux for 18 hours in 100 ml of acetic acid. After cooling to a temperature in the region of 20° C., the reaction mixture is concentrated to dryness under reduced pressure (15 mm Hg, 2 kPa) at 40° C. The product obtained is taken up in 200 ml of distilled water, then filtered and washed with 40 ml of isopropyl ether. After drying under reduced pressure (1 mm Hg; 0.13 kPa) at 40° C., 8.9 g of light-beige solid are obtained. 1 g of product is suspended in 7 ml of 0.1N sodium hydroxide solution and 13 ml of distilled water and stirred for 15 minutes, then filtered, washed with water and then with isopropyl ether and dried under reduced pressure (15 mm Hg, 2 kPa) at 20° C. 0.95 g of light-beige solid is obtained, which solid is purified by flash chromatography on a silica column, using a dichloromethane/methanol (90/10 by volume) mixture as eluent. 0.85 g of beige solid is obtained, which solid is suspended in 50 ml of ethyl ether and then filtered and dried under reduced pressure (15 mm Hg, 2 kPa) at 60° C. 0.58 g of the ethyl ester of (4,5-dihydro-4-oxo-10H-imidazo[1,2- a]indeno[1,2-e]pyrazin-9-yl)acetic acid is thus obtained in the form of a beige solid, the melting point of which is greater than 260° C. (Analysis: C17H15N3O3; % Calculated C: 66.01, H: 4.89, N: 13.58; % Found C: 65.89, H: 4.80, N: 13.20).

The ethyl ester of 1-(4-ethoxycarbonylmethyl-1- oxoindan-2-yl)imidazole-2-carboxylic acid can be prepared in the following way: 12.7 g of the ethyl ester of (2-bromo- 1-oxoindan-4-yl)acetic acid, 6 g of ethyl 1-H-imidazole-2- carboxylate and 28.5 g of potassium carbonate in 250 ml of acetone are brought to reflux for 3 hours and 30 minutes under an argon atmosphere. After cooling to a temperature in the region of 20° C., the precipitate formed is filtered and then washed with acetone. The filtrate is concentrated to dryness under reduced pressure (15 mm Hg, 2 kPa) at 40° C. The crude product is purified by flash chromatography on a silica column, using an ethyl acetate/methylene chloride (50/50 by volume) mixture as eluent. 10.15 g of the expected product are isolated in the form of a brown oil used as is in the subsequent syntheses.

The ethyl ester of (2-bromo-1-oxoindan-4-yl) acetic acid can be prepared in the following way: 2.15 ml of a solution of bromine in 20 ml of dichloromethane are added over 10 minutes, at a temperature in the region of 5° C. and under an argon atmosphere, to 10.45 g of the ethyl ester of (1-oxoindan-4-yl)acetic acid in 130 ml of dichloromethane. The reaction mixture is allowed to return to a temperature in the region of 20° C. and the reaction is continued for 2 hours. The reaction mixture is poured into 100 ml of water saturated with sodium chloride. The organic phase is washed with two times 100 ml of distilled water before being dried and concentrated, to result in 12.7 g of the expected product in the form of a brown oil used as is in the subsequent syntheses.

The ethyl ester of (1-oxoindan-4-yl)acetic acid can be prepared in the following way: 4.7 ml of oxalyl chloride are added at room temperature and under an argon atmosphere to 9.4 g of (1-oxoindan-4-yl)acetic acid in 200 ml of dichloromethane. After stirring for 4 hours at a temperature in the region of 20° C., 40 ml of ethanol are added to the reaction mixture and stirring is maintained for 1 hour. The organic phase is washed wih 2 times 25 ml of a saturated sodium hydrogencarbonate solution, then with 2 times 100 ml of distilled water and then dried and concentrated to result in 10.45 g of the expected product in the form of a brown oil used as is in the subsequent syntheses.

(1-Oxoindan-4-yl)acetic acid can be prepared in the following way: 43 g of 3-(2-(carboxymethyl)phenyl)propionic acid in 250 ml of sulphuric acid (95%) are heated at 100° C. for 18 hours. After cooling to a temperature in the region of 20° C., the reaction mixture is poured onto 1000 ml of ice-cold water. The mixture is extracted with three times 400 ml of ethyl acetate and the organic phase is washed with water, dried and concentrated to result in 9.56 g of an orange-coloured solid. The product thus obtained is suspended in 50 ml of petroleum ether, filtered, then washed with 25 ml of isopropyl ether and dried under reduced pressure (1 mm Hg; 0.13 kPa) at 60° C. to result in 6.7 g of an orange-yellow solid which melts at 160° C.

3-(2-(Carboxymethyl)phenyl)propionic acid can be prepared in the following way: 39.6 g of 3-(2-(carboxymethyl) phenyl)acrylic acid with 3 g of 10% palladium-on-charcoal in 400 ml of acetic acid are hydrogenated at a temperature in the region of 20° C. under a pressure of 1.2 bar for 4 hours. After filtering the reaction mixture, the organic phase is concentrated under reduced pressure (15 mm Hg; 2 kPa) at 40° C. The white solid obtained is suspended in 100 ml of petroleum ether and then filtered and dried under reduced pressure (1 mm Hg; 0.13 kPa) at 20° C. to result in 39.3 g of a white solid melting at 138° C.

3-(2-(Carboxymethyl)phenyl)acrylic acid can be prepared in the following way: 63.8 g of (2-bromophenyl)acetic acid, 25.5 ml of acrylic acid, 3.6 g of tri(2-tolyl)phosphine and 0.67 g of palladium acetate in 211 ml of tributylamine are heated at 100° C. for 6 hours. After cooling to a temperature in the region of 20° C., the reaction mixture is poured onto 420 ml of water and 80 ml of concentrated hydrochloric acid. The mixture is extracted with 3 times 500 ml of ethyl acetate; the organic phase is filtered, washed with 3 times 500 ml of water and then stirred in the presence of 800 ml of water and 35 g of sodium carbonate at a temperature in the region of 20° C. for 15 minutes. The aqueous phase is then acidified with 700 ml of 1N hydrochloric acid. The precipitate formed is filtered, washed with water and then dried under reduced pressure (1 mm Hg; 0.13 kPa) at 60° C. to result in 39.6 g of a white solid melting at 190° C.

EXAMPLE 3

A solution of 0.93 g of the ethyl ester of (4,5-dihydro-4-oxo-10H-imidazo[1,2-a]indeno[1,2-e]pyrazin-9-yl)acetic acid, 20 ml of methylamine as a 33% solution in ethanol and 20 ml of methanol under an argon atmosphere is stirred at a temperature in the region of 20° C. for 18 hours. The reaction mixture is filtered. The precipitate obtained is washed successively with three times 40 ml of ethanol and three times 40 ml of methyl-tert-butyl ether and dried under reduced pressure (15 mm Hg; 2 kPa) at 20° C. The solid obtained is suspended in a mixture of acetone (25 ml) and methanol (5 ml) and stirred for 15 minutes and then filtered, washed with 10 ml of acetone and dried under reduced pressure (1 mm Hg; 0.13 kPa) at 60° C. 0.32 g of N-methyl-2-(4,5-dihydro-4-oxo-10H-imidazo[1,2-a]indeno[1,2-e] pyrazin-9-yl) acetamide is obtained in the form of a white solid, the melting point of which is greater than 260° C. (Analysis C16H14N4O2; % Calculated C: 65.30, H: 4.79, N: 19.04; % Found C: 65.00, H: 4.50, N: 18.80).

EXAMPLE 4

A solution of 0.56 g of (4,5-dihydro-4-oxo-10H-imidazo [1,2-a]indeno[1,2-e]pyrazin-9-yl)acetic acid, 0.38 g of 1-(3-dimethylaminopropyl)-3-ethylcarbodiimide hydrochloride, 0.27 g of hydroxybenzotriazole and 1.1 ml of aniline in 20 ml of dimethylformamide is stirred under an argon atmosphere for 20 hours at a temperature in the region of 20° C. 20 ml of hydrochloric acid are added to the reaction mixture. The precipitate formed is filtered, washed with water and with isopropyl ether and then dried under reduced pressure (15 mm Hg; 2 kPa) at 20° C. The beige solid obtained is suspended in a solution of 20 ml of water and 84 mg of sodium hydrogencarbonate and then filtered and washed with water. The solid obtained is resuspended in 10 ml of 0.1N hydrochloric acid and then filtered, washed with water and dried under reduced pressure (1 mm Hg; 0.13 kPa) at 60° C. 0.2 g of N-phenyl-2-(4,5-dihydro-4-oxo-10H-imidazo[1,2-a]indeno[1,2-e]pyrazin-9-yl)acetamide is obtained in the form of a white solid melting at a temperature greater than 260° C. (Analysis C21H16N4O2; % Calculated C: 70.77, H: 4.53, N: 15.72; % Found C: 70.74, H: 4.39, N: 15.64).

EXAMPLE 5

A mixture of 0.25 g of 9-cyano-5H,10H-imidazo[1,2-a] indeno[1,2-e]pyrazin-4-one, 10 ml of acetic acid, 10 ml of trifluoroacetic acid and 20 mg of 10% palladium-on-charcoal is hydrogenated in an autoclave under a pressure of 50 bar for 20 hours. The suspension is filtered and washed with acetic acid. The filtrate is concentrated to dryness under reduced pressure (15 mm Hg; 2 Kpa) at 40° C. The solid obtained is dissolved in a mixture of 50 ml of acetic acid and 10 ml of concentrated hydrochloric acid and then again concentrated to dryness under reduced pressure (15 mm Hg; 2 kPa) at 40° C. The residue obtained, taken up in 25 ml of methanol, is filtered, then washed with two times 25 ml of isopropyl ether and dried under reduced pressure (1 mm Hg; 0.13 kPa) at 20° C. 0.24 g of 9-aminomethyl-5H,10H-imidazo[1,2-a]indeno[1,2-e]pyrazin-4-one dihydrochloride is obtained in the form of a white solid melting above 260° C. (Analysis C14H14Cl2N4;0% Calculated C: 51.71, H: 4.34, N: 17.23; % Found C: 52.11, H: 4.53, N: 17.04).

9-Cyano-5H,10H-imidazo[1,2-a]indeno[1,2-e]pyrazin-4-one can be obtained in the following way: 1 g of 1-[(4-cyano-1-oxoindan-2-yl)]imidazole-2-carboxamide is dissolved in 10 ml of acetic acid and the solution is brought to reflux for 22 hours. After cooling the reaction mixture, the suspension is filtered and washed with 5 ml of acetic acid, distilled water and ethyl ether. The solid is dried under reduced pressure (15 mm Hg; 2 kPa) at 30° C. and 0.4 g of 9-cyano-5H,10H-imidazo[1,2-a]indeno[1,2-e]pyrazine-4-one is thus obtained, which product melts at a temperature greater than 260° C. (Analysis C14H8N4O1·0.21H2O; % Calculated C: 67.74, H: 3.25, N: 22.57, O: 6.45; % Found C: 68.1, H: 3.3, N: 22.6, O: 6.7).

1-[(4-Cyano-1-oxoindan-2-yl)]imidazole-2-carboxamide can be obtained in the following way: a solution of 1.5 g of ethyl 1-[(4-cyano-1-oxoindan-2-yl)]imidazole-2-carboxylate in 130 ml of methanol is kept saturated for one hour at a temperature in the region of 20° C. with a stream of gaseous ammonia. The reaction mixture is then concentrated to dryness under reduced pressure (15 mm Hg; 2 kPa) at 50° C. 1.2 g of 1-[(4-cyano-1-oxoindan-2-yl)]imidazole-2-carboxamide are thus obtained, which product melts at 216° C.

Ethyl 1-[(4-cyano-1-oxoindan-2-yl)]imidazole-2-carboxylate can be obtained in the following way: a mixture of 3.92 g of ethyl imidazole-2-carboxylate and 3.4 g of 2-bromo-4-cyano-1-indanone is heated at 130° C. for 20 minutes, cooled to 20° C. and dissolved in 20 ml of dichloromethane. The mixture is then concentrated to dryness under reduced pressure (15 mm Hg; 2 kPa) at 40° C. The residue thus obtained is purified by flash chromatography on a silica column, under a nitrogen stream at medium pressure (0.5 bar), with a dichloromethane/methanol (95/5 by volume) mixture as eluent. 1.5 g of ethyl 1-[(4-cyano-1-oxoindan-2-yl)]imidazole-2-carboxylate are thus obtained, which product melts at 159° C.

2-Bromo-4-cyano-1-indanone can be obtained in the following way: a solution of 6.9 g of 4-cyano-1-indanone and 95 ml of chloroform is cooled to 5° C. A solution of 7.04 g of bromine and 20 ml of chloroform is then added dropwise over two hours at a temperature of between 0 and 5° C. After having left the reaction mixture stirring for one hour, the temperature of introduction being retained, the solution is allowed to return to room temperature and stirring is continued overnight. The reaction mixture is then concentrated to dryness under reduced pressure (15 mm Hg; 2 kPa) at 40° C. The residue thus obtained is purified by flash chromatography on a silica column, under a nitrogen stream at medium pressure (0.5 bar), with an ethyl ether/cyclohexane (20/80 by volume) mixture as eluent. 3.43 g of 2-bromo-4-cyano-1-indanone are thus obtained, which product melts at 124° C.

4-Cyano-1-indanone can be prepared in the following way: 12.61 g of copper cyanide are added to a solution of 10 g of 4-bromo-1-indanone in 94 ml of dimethylformamide and the reaction mixture is then brought to reflux for 6 hours and stirred at a temperature in the region of 20° C. overnight. The solution is then poured into an aqueous sodium cyanide solution (5%), stirred for 15 minutes and extracted with three times 500 ml of ethyl acetate. The organic phases are dried over sodium sulphate and concentrated under reduced pressure (15 mm Hg; 2 kPa) at 40° C. The residue thus obtained is purified by flash chromatography on a silica column, under a nitrogen stream at medium pressure (0.5 bar), with an ethyl acetate/cyclohexane (20/80 by volume) mixture as eluent. 5.9 g of 4-cyano-1-indanone are thus obtained, which product melts at 122° C.

4-Bromo-1-indanone can be prepared as described by F. G. Holliman, F. G. Manne and D. A. Thornton, J. Chem. Soc., 9 (1960).

EXAMPLE 6

A mixture of 1 g of 9-aminomethyl-5H,10H-imidazo[1,2-a]indeno[1,2-e]pyrazin-4-one and 20 ml of acetic anhydride is stirred under an argon atmosphere for 2 hours at a temperature in the region of 20° C. The reaction mixture is filtered and the insoluble material is washed successively with 10 ml of acetic anhydride and two times 40 ml of methyl-tert-butyl ether and then dried under reduced pressure (15 mm Hg; 2 kPa) at 20° C. The white solid is suspended in a mixture of acetone (30 ml) and methanol (5 ml), then filtered and dried under reduced pressure (1 mm Hg; 0.13 kPa) at 60° C. 1.03 g of N-[(4,5-dihydro-4-oxo-10H-imidazo[1,2-a]indeno[1,2-e]pyrazin-9-yl) methyl] acetamide are obtained in the form of a white solid, the melting point of which is greater than 260° C. (Analysis C16H14N402; % Calculated C: 65.30, H: 4.79, N: 19.04; % Found C: 65.20, H: 5.10, N: 19.30).

EXAMPLE 7

A suspension of 0.25 g of 9-aminomethyl-5H,10H-imidazo[1,2-a]indeno[1,2-e]pyrazin-4-one, 0.49 g of 4-nitrophenyl N-methylcarbamate and 10 ml of dimethylformamide under an argon atmosphere is stirred for 4 hours at a temperature in the region of 20° C. The reaction mixture is filtered, washed successively with 5 ml of dimethylformamide and two times 20 ml of methyl-tert-butyl ether and then dried under reduced pressure (1 mm Hg; 0.13 kPa) at 60° C. 0.2 g of 9-[(3-methylureido)methyl]-5H,10H-imidazo[1,2-a]indeno[1,2-e]pyrazin-4-one is obtaine in the form of a white solid, the melting point of which is greater than 260° C. (Analysis C16H15N502; % Calculated C: 62.13, H: 4.89, N: 22.64; % Found C: 62.03, H: 4.90, N: 22.26).

EXAMPLE 8

A mixture of 24.5 g of ethyl 1-(5-ethoxycarbonylmethyl-1-oxoindan-2-yl)imidazole-2-carboxylate and 236.5 g of ammonium acetate in 1 liter of acetic acid is brought to reflux for 8 hours. After evaporation of the acetic acid under reduced pressure, 1 liter of distilled water is added to the residue. The insoluble material is filtered, washed with water and then air-dried. 10.6 g of a grey solid are thus obtained. Recrystallization from 175 ml of ethanol of a 0.8 g sample of this solid results, after drying at 60° C. under reduced pressure (1 mbar), in 0.65 g of ethyl [4,5-dihydro-4-oxo-10H-imidazo[1,2-a]indeno[1,2-e]pyrazin-8-yl]acetate in the form of a brown solid with a melting point greater than 260° C. (Analysis; % Calculated C: 66.01, H: 4.89, N: 13.58, O: 15.52; % Found C: 65.8, H: 5.1, N: 13.2, O: 15.5).

Ethyl 1-(5-ethoxycarbonylmethyl-1-oxoindan-2-yl) imidazole-2-carboxylate can be synthesized as follows: a suspension, under a nitrogen stream, of 47 g of ethyl imidazole-2-carboxylate and 50 g of a 60/40 molar mixture of 2-bromo-5-ethoxycarbonylmethylindan-1-one and 2,2-dibromo-5-ethoxycarbonylmethylindan-1-one in 1.5 liter of toluene is heated at reflux for 26 hours. The solvent is evaporated under reduced pressure and the crude reaction product is taken up in a mixture of 1.5 liter of dichloromethane and 500 ml of distilled water. The aqueous phase is removed and the organic phase is washed successively three times with 500 ml of distilled water, once with 500 ml of saturated potassium carbonate solution and once with 500 ml of distilled water and it is then dried over magnesium sulphate and evaporated under reduced pressure. After purification of the residue by flash chromatography on a silica column (eluent: dichloromethane/ethyl acetate (1/1 by volume)), 21.3 g of ethyl 1-(5-ethoxycarbonylmethyl-1-oxoindan-2-yl)imidazole-2-carboxylate are obtained in the form of a 70% pure brown solid which is used as is in the subsequent operations (Rf=0.35, silica gel thin layer chromatography, eluent: ethyl acetate/dichoromethane (1/1 by volume)) ($^1$H NMR spectrum in CDCl$_3$, T=300K, δ in ppm: 1.20 (3H, t, J=6 Hz, CH$_3$), 1.28.(3H, t, J=6 Hz, CH$_3$), 3.20 and 3.76 (each 1H, respectively dd, J=6 and 16 Hz, and dd, J=8 and 16 Hz, CH$_2$), 3.67 (2H, s, CH$_2$), 4.10 (2H, q, J=6 Hz, OCH$_2$), 4.23 (2H, q, J=6 Hz, OCH$_2$), 5.81 (1H, t, J=6 Hz, CH), 6.99 (1H, s, CH), 7.13 (1H, s, CH), 7.32 (1H, d, J=7 Hz, CH), 7.37 (1H, s, CH), 7.71 (1H, d, J=7 Hz, CH)).

Ethyl imidazole-2-carboxylate can be obtained as described in U.S. Pat. No. 3,600,399.

2-Bromo-5-ethoxycarbonylmethylindan-1-one can be prepared in the following way: 8.9 ml of bromine in solution in 87 ml of dichloromethane are added dropwise to a solution of 38 g of 5-ethoxycarbonylmethylindan-1-one in a mixture of 175 ml of dichloromethane and 350 ml of absolute ethanol maintained at a temperature of between 5 and 10° C. The reaction is continued for 1 hour and 30 minutes at a temperature of between 5 and 10° C. and then for 15 minutes at a temperature in the region of 20° C. The reaction mixture is then evaporated and the residue is taken up in 500 ml of dichloromethane. The organic phase is washed successively three times with 200 ml of distilled water, once with 200 ml of saturated sodium hydrogencarbonate solution and twice with 200 ml of distilled water and then dried over magnesium sulphate and evaporated. 50.1 g of a mixture of 2-bromo-5-ethoxycarbonylmethylindan-1-one (Rf=0.41, silica gel thin layer chromatography, eluent: dichloromethane) and 2,5-dibromo-5-ethoxycarbonylmethylindan-1-one (Rf=0.59, silica gel thin layer chromatography, eluent: dichloromethane) are thus obtained, which mixture is used as is in the continuation of the synthesis (monobrominated compound/dibrominated compound molar ratio: 60/40) ($^1$H NMR spectrum of 2-bromo-5-ethoxycarbonylmethylindan-1-one in CDCl$_3$, T=300K, δ in ppm: 1.25 (3H, t, J=6 Hz, CH$_3$), 3.39 and 3.80 (each 1H, respectively dd, J=4 and 16 Hz, and dd, J=7 and 16 Hz, CH$_2$), 3.72 (2H, m, CH$_2$), 4.06 (2H, q, J=6 Hz, OCH$_2$), 4.65 (1H, dd, J=4 and 7 Hz, CH), between 7.30 and 7.45 (2H, m, arom. H), 7.79 (1H, d, J=7 Hz, arom. H)).

5-Ethoxycarbonylmethylindan-1-one can be prepared as follows: a solution of 39.9 g of (1-oxoindan-5-yl)acetic acid and 79.8 ml of methanesulphonic acid in 720 ml of absolute ethanol is heated for 2 hours at reflux. The ethanol is evaporated and the residue is taken up in 500 ml of dichloromethane. The organic phase thus obtained is washed successively four times with 200 ml of distilled water, once with 200 ml of saturated aqueous sodium hydrogencarbonate solution and once with 200 ml of distilled water, dried over magnesium sulphate and evaporated. 41.5 g of ethyl (1-oxoindan-5-yl)acetate are thus obtained in the form of a cream solid ($^1$H NMR spectrum in CDCl$_{31}$, T=300 K, δ in ppm: 1.25 (3H, t, J=6 Hz, CH$_3$), 2.66 (2H, m, COCH$_2$), 3.12 (2H, t, J=5 Hz, CH$_2$), 3.70 (2H, s, CH$_2$), 4.16 (2H, t, J=6 Hz, OCH$_2$), 7.26 (1H, d, J=7 Hz, arom. CH), 7.40 (1H, s, arom. CH), 7.69 (1H, d, J=7 Hz, arom. CH)).

(1-Oxoindan-5-yl)acetic acid can be obtained in the following way: a solution of 50.9 g of ethyl [4-(3-chloro-1-oxopropyl)phenyl]acetate in 950 ml of 95% sulphuric acid is heated for 1 hour at 100° C. The reaction mixture is cooled to a temperature in the region of 20° C. and then poured into 4 liters of ice-cold water. The mixture is extracted three times with 1.5 liter of dichloromethane. The organic phase is washed three times with 1 liter of water, then dried over magnesium sulphate and evaporated under reduced pressure. 22.2 g of (1-oxoindan-5-yl)acetic acid are thus obtained in the form of a cream solid melting at 141° C. ($^1$H NMR spectrum in CDCl$_3$, T=300 K, δ in ppm: 2.70 (2H, m, COCH$_2$), 3.12 (2H, t, J=5 Hz, CH$_2$), 3.68 (2H, s, CH$_2$), 7.27 (1H, d, J=7 Hz, arom. CH), 7.45 (1H, s, arom. CH), 7.76 (1H, d, J=7 Hz, arom. CH)).

Ethyl [4-(3-chloro-1-oxopropyl)phenyl]acetate can be synthesized in the following way: a solution of 600 g of ethyl phenylacetate and 384 ml of 3-chloropropionyl chloride in 1 liter of dichloromethane is added dropwise, so that the temperature of the reaction mixture does not exceed 25° C., to a suspension of 1.5 kg of aluminium chloride in 3.5 liters of dichloromethane. After reacting for 24 hours at a temperature in the region of 20° C., the reaction mixture is poured onto 8 liters of ice-cold water. The organic phase is separated by settling and the aqueous phase is extracted twice with 2 liters of dichloromethane. The organic phases are combined, washed four times with 2 liters of distilled water, dried over magnesium sulphate and evaporated. After filtration of the residue on a silica column (eluent: dichloromethane), 605 g of an oil are obtained, which oil crystallizes. After washing with absolute ethanol and drying, 82 g of ethyl [4-(3-chloro-1-oxopropyl)phenyl]acetate are obtained in the form of a white solid melting at 69° C. ($^1$H NMR spectrum in CDCl$_3$, T=300 K, δ in ppm: 1.26 (3H, t, J=6 Hz, CH$_3$), 3.43 (2H, t, J=6 Hz, CH$_2$Cl), 3.68 (2H, s, CH$_2$), 3.92 (2H, t, J=6 Hz, CH$_2$) 4.16 (2H, q, J=6 Hz, OCH$_2$), 7.40 (2H, d, J=7 Hz, arom. CH), 7.92 (2H, d, J=7 Hz, arom. CH)).

EXAMPLE 9

A suspension of 0.5 g of ethyl [4,5-dihydro-4-oxo-10H-imidazo[1,2-a]indeno[1,2-e]pyrazin-8-yl]acetate in 50 ml of 6N hydrochloric acid is heated at reflux for 2 hours. 25 ml of 1,4-dioxane are added to the mixture and reflux is continued for 4 hours. After returning to a temperature in the region of 20° C., the solid formed is filtered, washed with 5 ml of 1,4-dioxane and then dried under reduced pressure (1 mbar) at 60° C. 0.47 g of [4,5-dihydro-4-oxo-10H-imidazo[1,2-a]indeno[1,2-e]pyrazin-8-yl]acetic acid is thus obtained in the form of a hydrochloride monohydrate, the melting point of which is greater than 260° C. (Analysis; % Calculated C: 56.7, H: 3.81, Cl: 11.16, N: 13.23; % Found C: 56.7, H: 3.9, Cl: 10.9, N: 12.9).

EXAMPLE 10

A mixture of 0.618 g of ethyl [4,5-dihydro-4-oxo-10H-imidazo[1,2-a]indeno[1-,2-e]pyrazin-8-yl]acetate and 10 ml of benzylamine is heated at 140° C. for 17 hours under a nitrogen atmosphere. After returning to room temperature, 50 ml of dichloromethane are added to the reaction mixture. The solid formed is filtered, washed with dichloromethane and then recrystallized from 25 ml of dimethylformamide. After drying under reduced pressure (1 mbar) at 60° C., 0.65 g of N-benzyl-2-(4,5-dihydro-4-oxo-10H-imidazo[1,2-a]indeno[1,2-e]pyrazin-8-yl)acetamide is thus obtained, which product has a melting point greater than 260° C. (Analysis; % Calculated C: 71.34, H: 4.90, N: 15.13, O: 8.64; % Calculated C: 71.1, H: 5.0, N: 15.2, O: 9.1).

EXAMPLE 11

1.21 ml of triethylamine are added to a suspension, under nitrogen, of 2.9 g of [4,5-dihydro-4-oxo-10H-imidazo[1,2-a]indeno[1,2-e]pyrazin-8-yl]acetic acid hydrochloride and 108 ml of dimethylformamide. After stirring for 30 minutes at a temperature in the region of 20° C., 3.5 g of 1,1'-carbonyldiimidazole are added to the reaction mixture and stirring is continued for 2 hours at a temperature in the region of 20° C. The reaction mixture is then cooled to −10° C. and a stream of gaseous ammonia is passed into the mixture for 15 minutes. After returning to a temperature in the region of 20° C., the reaction mixture is concentrated to dryness under reduced pressure. The evaporation residue is taken up in 100 ml of distilled water and the suspended solid is filtered, washed with water and then dissolved in 125 ml of dimethyl sulphoxide. The addition of 250 ml of acetone to the solution causes the appearance of a precipitate which is collected by filtration, washed with acetone and dried under reduced pressure (1 mbar) at 60° C. 1.1 g of [4,5-dihydro-4-oxo-10H-imidazo[1,2-a]indeno[1,2-e]pyrazin-8-yl]acetamide are thus obtained in the form of a beige solid with a melting point greater than 260° C. (Analysis; % Calculated C: 64.28, H: 4.32, N: 19.99, O: 11.42; % Found C: 63.9, H: 4.3, N: 19.8, O: 10.9).

EXAMPLE 12

A mixture of 1.8 g of ethyl 1-(5-N-methylcarboxamidomethyl-1-oxoindan-2-yl)imidazole-2-carboxylate and 20.9 g of ammonium acetate in 88 ml of acetic acid is brought to reflux for 2 hours. The reaction mixture is concentrated to dryness under reduced pressure. The evaporation residue is taken up in 100 ml of distilled water. The suspended solid is filtered, washed with distilled water and then recrystallized from 25 ml of acetic acid. After drying under reduced pressure (1 mbar) at 60° C., 0.75 g of N-methyl-[4,5-dihydro-4-oxo-10H-imidazo[1,2-a]indeno[1,2-e]pyrazin-8-yl]acetamide is obtained in the form of a beige solid with a melting point greater than 260° C. (Analysis; % Calculated C: 65:30, H: 4.79, N: 19.04, O: 10.87; % Found C: 65.5, H: 4.8, N: 18.9, O: 11.2).

Ethyl 1-(5-N-methylcarboxamidomethyl-1-oxoindan-2-yl)imidazole-2-carboxylate can be obtained in the following way: a mixture of 1.44 g of ethyl imidazole-2-carboxylate, 3.55 g of potassium carbonate and 68 mg of crown ether 18C-6 in 130 ml of dimethylformamide is heated for 2 hours at 85° C. and then cooled to 20° C. A solution of 2.9 g of N-methyl-(2-bromo-1-oxoindan-5-yl)acetamide is then added to the reaction mixture. The reaction is continued for 16 hours at a temperature in the region of 20° C. and then for 1 hour at 80° C. The dimethylformamide is removed under reduced pressure and the residue is taken up in 100 ml of distilled water and 200 ml of ethyl acetate. The aqueous phase is extracted four times with 200 ml of ethyl acetate. The organic phases are combined, washed four times with 100 ml of water, dried over magnesium sulphate and evaporated. 1.4 g of ethyl 1-(5-N-methylcarboxamidomethyl-1-oxoindan-2-yl)imidazole-2-carboxylate are thus obtained in the form of a brown solid (Rf=0.39, silica gel thin layer chromatography, eluent: ethyl acetate/methanol (8/2 by volume)).

N-Methyl(2-bromo-1-oxoindan-5-yl)acetamide can be synthesized as follows: a solution of 9 g of N-methyl(1-oxoindan-5-yl)acetamide in 200 ml of dichloromethane and 500 ml of absolute ethanol is cooled to a temperature of between 0 and 5° C. 7.1 g of bromine, diluted in 100 ml of dichloromethane, are added dropwise to the reaction mixture, so that the temperature does not exceed 5° C. After stirring for 1 hour and 30 minutes at a temperature in the region of 20° C., the solvent is evaporated under reduced pressure. The crude reaction product is purified by flash chromatography on silica (eluent: dichloromethane/methanol (96/4 by volume)). 7.8 g of N-methyl(2-bromo-1-oxoindan-5-yl)acetamide are thus obtained in the form of a white solid melting at 184° C. ($^1$H NMR spectrum in d6-DMSO, T 300 K, δ in ppm: 2.60 (3H, d, J=5 Hz, NCH$_3$), 3.35 and 3.90 (each 1H, respectively m, and dd, J=6 and 16 Hz, CH$_2$), 3.56 (2H, d, COCH$_2$), 5.01 (1H, dd, J=2 and 6 Hz, CHBr), 7.40 (1H, d, J=7 Hz, arom. CH), 7.45 (1H, s, arom. CH), 7.70 (1H, d, J=7 Hz, arom. CH), 8.05 (1H, broad s, NH)).

N-Methyl(1-oxoindan-5-yl)acetamide can be obtained in the following way: 16 g of N,N'-carbonyldiimidazole are added portionwise to a solution of 12.5 g of (1-oxoindan-5-yl)acetic acid in 250 ml of tetrahydrofuran maintained at 0C. After reacting for 1 hour at a temperature in the region of 20° C., the solution is cooled to −10° C. and a stream of monomethylamine is passed into the mixture for 5 minutes. After returning to a temperature in the region of 20° C., the reaction mixture is evaporated under reduced pressure. The residue is taken up in 1 liter of dichloromethane. The organic phase is washed three times with 500 ml of distilled water, dried over magnesium sulphate and then evaporated. The resulting brown solid is purified by flash chromatography on silica (eluent dichloromethane/methanol (96/4 by volume)). 9 g of N-methyl(1-oxoindan-5-yl)acetamide are thus obtained in the form of a white solid melting at 169° C. ($^1$H NMR spectrum in CDCl$_3$, T=300 K δ in ppm: 2.69 (2H$_1$ m, COH$_2$), 2.80 (3H, d, NCH$_3$), 3.14 (2H, t, J=5 Hz, CH$_2$), 3.65 (2H, 5, H$_2$), 5.47 (1H, broad s, NH), 7.26 (1H, d, J=7 Hz, arom. CH), 7.42 (1H, s, arom. CH), 7.74 (1H, d, J=7 Hz, arom. CH)).

EXAMPLE 13

A suspension, under nitrogen, of 1 g of ethyl 8-N-methylcarboxamidomethyl-4,5-dihydro-4-oxo-10H-imidazo[1,2-a]indeno[1,2-e]pyrazin-2-carboxylate, 97 ml of 1,4-dioxane and 24 ml of distilled water is dissolved by addition of 7.26 ml of 1N sodium hydroxide solution. The mixture is stirred for 18 hours at a temperature in the region of 20° C. The reaction mixture is acidified with 1N hydrochloric acid to pH 1. The solid obtained is filtered and washed successively with 1,4-dioxane, distilled water and ethyl ether. After drying under reduced pressure (1 mbar) at 60° C., 0.75 g of 8-N-methylcarboxamidomethyl-4,5-dihydro-4-oxo-10H-imidazo[1,2-a]indeno[1,2-e]pyrazin-2-carboxylic acid is obtained in the form of a yellow solid with a melting point greater than 260° C. (Analysis; % Calculated C: 60.35, H: 4.17, N: 16.56; % Found C: 60.4, H: 4.1, N: 16.6).

Ethyl 8-N-methylcarboxamidomethyl-4,5-dihydro-4-oxo-10H-imidazo[1,2-a]indeno[1,2-e]pyrazin-2-carboxylate can be synthesized in the following way: a mixture of 3.4 g of diethyl 1-[5-(N-methylcarboxamidomethyl)-1-oxoindan-2-yl]imidazole-2,4-dicarboxylate and 33.2 g of ammonium acetate in 137 ml of glacial acetic acid is heated at reflux for 16 hours. After removal of the solvent by evaporation under reduced pressure, 100 ml of distilled water are added to the residue. The precipitate formed is collected by filtration and then washed with 50 ml of distilled water and with 50 ml of acetone. 2 g of ethyl 8-N-methylcarboxamidomethyl-4,5-dihydro-4-oxo-10H-imidazo[1,2-a]indeno[1,2-e]pyrazin-2-carboxylate are thus obtained in the form of a beige solid melting above 260° C.

Diethyl 1-[5-(N-methylcarboxamidomethyl)-1-oxoindan-2-yl]imidazole-2,4-dicarboxylate can be prepared in the following way: a mixture of 2.6 g of diethyl imidazole-2,4-dicarboxylate, 4.2 g of potassium carbonate and 79 mg of crown ether 18C-6 in 150 ml of dimethylformamide is heated for 2 hours at 85° C. and then cooled to a temperature in the region of 20° C. A solution of 3.4 g of N-methyl(2-bromo-1-oxoindan-5-yl)acetamide in 75 ml of dimethylformamide is then added to the reaction mixture. The reaction is continued for 16 hours at a temperature in the region of 20° C. The dimethylformamide is removed under reduced pressure and the residue is taken up in 150 ml of distilled water and 200 ml of ethyl acetate. The organic phase is separated by settling and the aqueous phase is extracted four times with 200 ml of ethyl acetate. The organic phases are combined, washed three times with 100 ml of distilled water, dried over magnesium sulphate and evaporated. 2.9 g of diethyl 1-[5-(N-methylcarboxamidomethyl)-1-oxoindan-2-yl]imidazole-2,4-dicarboxylate are thus obtained in the form of a cream solid ($^1$H NMR spectrum in d6-DMSO, T=300 K, δ in ppm 1.25 (3H, t, J=6 Hz, CH$_3$), 1.37 (3H, t, J=6 Hz, CH$_3$), 2.66 (3H, d, J=4 Hz, NCH$_3$), 3.49 and 3.80 (each 1H, respectively dd, J=6 and 16 Hz, and dd, J=8 and 16 Hz, CH$_2$), 3.62 (2H, s, CH$_2$), 4.20 (2H, q, J=6 Hz, OCH$_2$), 4.37 (2H, q, J=6 Hz, OCH$_2$), 5.90 (1H, dd, J=6 and 8 Hz, CH), 7.47 (1H, d, J=7 Hz, CH), 7.55 (1H, s, CH), 7.76 (1H, d, J=7 Hz, CH), 8.17 (1H, s, NH), 8.40 (1H, s, CH)).

Diethyl imidazole-2,4-dicarboxylate can be synthesized as described by P. S. Branco et al., Tetrahedron, 48 (30), 6335 (1992).

EXAMPLE 14

A mixture of 0.5 g of ethyl 8-(N-methylcarboxamidomethyl)-4,5-dihydro-4-oxo-10H-imidazo[1,2-a]indeno[1,2-e]pyrazin-2-carboxylate, 25 ml of dioxane and 50 ml of 6N hydrochloric acid is heated at reflux for 5 hours. After cooling the reaction mixture, the precipitate formed is filtered and washed with 50 ml of distilled water and 10 ml of dioxane. 320 mg of 8-carboxymethyl-4,5-dihydro-4-oxo-10H-imidazo[1,2-a]indeno[1,2-e]pyrazin-2-carboxylic acid hydrochloride are thus obtained ($^1$H NMR spectrum in d6-DMSO, T=300 K, δ in ppm: 3.62 (2H, s, $CH_2CO$), 3.97 (2H, s, $CH_2$), 7.25 (1H, d, J=7 Hz, arom. H), 7.45 (1H, s, arom. CH), 7.78 (1H, d, J=7 Hz, arom. CH), 8.48 (1H, s, arom. CH), 12.5 (1H, s, NH)).

EXAMPLE 15

A mixture of 1 g of 8-aminomethyl-5H,10H-imidazo[1,2-a]indeno[1,2-e]pyrazin-4-one and 1.8 g of 4-nitrophenyl-N-methylcarbamate in 40 ml of dimethylformamide is stirred for 18 hours at a temperature in the region of 20° C. The reaction mixture is filtered and washed with 5 ml of dimethylformamide. The solid is taken up in 25 ml of dimethylformamide and the suspension is heated at 100° C. for 30 minutes. The insoluble material is filtered and washed with 5 ml of dimethylformamide and then with 20 ml of acetone. After drying under reduced pressure (1 mbar) at 60° C., 1.2 g of 8-(3-methylureido)methyl-5H,10H-imidazo[1,2-a]indeno[1,2-e]pyrazin-4-one are obtained in the form of a yellow solid, the melting point of which is greater than 260° C. (Analysis; % Calculated C: 62.13, H: 4.89, N: 22.64; % Found C: 62.0, H: 4.5, N: 22.6).

4-Nitrophenyl-N-methylcarbamate can be prepared as described by T. Konakahara et al., Synthesis, 103 (1993).

8-Aminomethyl-5H,10H-imidazo[1,2-a]indeno[1,2-e]pyrazin-4-one can be prepared in the following way: a mixture of 1 g of 8-phthalimidomethyl-5H,10H-imidazo[1,2-a]indeno[1,2-e]pyrazin-4-one, 50 ml of absolute ethanol, 20 ml of distilled water and 1.3 ml of hydrazine hydrate is heated at reflux for 18 hours. The solid is filtered and washed with distilled water. It is then stirred in 15 ml of 2N hydrochloric acid for 1 hour and 30 minutes at a temperature in the region of 20° C., filtered and rinsed with water and then with acetone. The product is taken up in 50 ml of dimethylformamide, stirred for 1 hour and 30 minutes at 120° C. and the suspension is filtered while hot. The insoluble material is washed with dimethylformamide and then with acetone and dried at 60° C. under reduced pressure (1 mbar). 0.58 g of 8-aminomethyl-5H,10H-imidazo[1,2-a]indeno[1,2-e]pyrazin-4-one hydrochloride is thus obtained in the form of a beige solid with a melting point greater than 260° C. (Analysis; % Calculated C: 58.24, H: 4.54, Cl: 12.28, N: 19.40; % Found C: 58.3, H: 4.8, Cl: 12.2, N: 19.2).

8-Phthalimidomethyl-5H,10H-imidazo[1,2-a]indeno[1,2-e]pyrazin-4-one can be obtained in the following way: a mixture of 17 g of ethyl 1-(5-phthalimidomethyl-1oxoindan-2yl)imidazole-2-carboxylate and 153 g of ammonium acetate in 355 ml of glacial acetic acid is heated at reflux for 16 hours. The reaction mixture is cooled to a temperature in the region of 20° C. The precipitate is filtered on sintered glass, rinsed with distilled water to neutral pH and then washed with acetone. After drying under vacuum (1 mbar) at 80° C., 10 g of 8-phthalimidomethyl-5H,10H-imidazo[1,2-a]indeno[1,2-e]pyrazin-4-one are obtained in the form of a brown solid ($^1$H NMR spectrum in d6-DMSO, T=300 K, δ in ppm: 4.00 (2H, s, $CH_2$), 4.83 (2H, s, $NCH_2$), 7.47 (1H, d, J=7 Hz, arom. CH), 7.55 (2H, d, J=7 Hz, arom. CH), 7.80 (1H, d,J=7 Hz, arom. CH), between 7.85 and 8.00 (4H, m, phthal. H), 12.30 (1H, broad s, NH)).

Ethyl 1-(5-phthalimidomethyl-1oxoindan-2yl)imidazole-2-carboxylate can be synthesized in the following way: a suspension of 28.3 g of 2-bromo-5-phthalimidomethylindan-1-one and 21.4 g of ethyl imidazole-2-carboxylate in 700 ml of toluene is heated at reflux for 24 hours. The solution is evaporated under reduced pressure and the residue is taken up in 800 ml of saturated potassium carbonate solution and 800 ml of dichloromethane. The organic phase is separated by settling and the aqueous phase is extracted twice with 500 ml of-dichloromethane. The organic phases are combined, washed six times with 800 ml of distilled water, dried over magnesium sulphate and evaporated under reduced pressure. After purification of the residue by flash chromatography on a silica column (eluent: dichloromethane/methanol (99/1 by volume)), 17.5 g of ethyl 1-(5-phthalimidomethyl-1oxoindan-2yl)imidazole-2-carboxylate are obtained in the form of a beige solid ($^1$H NMR spectrum in d6-DMSO and a few drops of $CD_3CO_2D$, T=300 K, δ in ppm: 1.15 (3H, t, J=7 Hz, $CH_3$), 3.35 and 3.70 (each 1H, respectively dd, J=6 and 16 Hz, and dd, J=9 and 16 Hz, $CH_2$), 4.10 (2H, q, J=7 Hz, $OCH_2$), 4.93 (2H, s, $NCH_2$), 5.79 (1H, dd, J=6 and 9 Hz, NCH), 7.20 (1H, s, CH), 7.48 (1H, d, J=7 Hz, arom. CH), 7.53 (1H, s, arom. CH), 7.56 (1H, s, arom. CH), 7.72 (1H, d, J=7 Hz, arom. CH), between 7.80 and 7.95 (4H, m, phthal. H)).

2-Bromo-5-phthalimidomethylindan-1-one can be prepared as follows: 15.5 g of bromine, diluted in 75 ml of dichloromethane, are added to a solution of 22.6 g of 5-phthalimidomethylindan-1-one in 150 ml of dichloromethane kept at a temperature of between 0 and 5° C. After 16 hours at a temperature in the region of 20° C., the reaction mixture is poured onto 300 ml of distilled water. The organic phase is separated by settling and the aqueous phase is extracted three times with 100 ml of dichloromethane. The organic phases are combined, washed twice with 100 ml of distilled water, dried over magnesium sulphate and evaporated under reduced pressure. 28.3 g of 2-bromo-5-phthalimidomethylindan-1-one are thus obtained in the form of a beige solid ($^1$H NMR spectrum in d6-DMSO, T=300 K, δ in ppm: 3.30 and 3.87 (each 1H, respectively dd, J=4 and 16 Hz, and dd, J=7 and 16 Hz, $CH_2$), 4.90 (2H, s, $NCH_2$), 4.99 (1H, dd, J=4 and 7 Hz, CHBr), 7.46 (1H, d, J=7 Hz, arom. CH), 7.51 (1H, s, arom. CH), 7.75 (1H, d, J=7 Hz, arom. CH), between 7.85 and 8.00 (4H, m, phthal. H)).

5-Phthalimidomethylindan-1-one can be obtained as described below: 20.4 ml of thionyl chloride and a few drops of dimethylformamide are added to a suspension of 43.1 g of 3-[3-(phthalimidomethyl)phenyl]propanoic acid in 900 ml of dichloromethane. The mixture is stirred for 2 hours at 30° C. and then for 16 hours at a temperature in the region of 20° C. Evaporation of the solvent results in 46.3 g of a yellow oil being obtained. This oil is dissolved in 400 ml of 1,2-dichloroethane and added dropwise to a suspension of 56 g of aluminium chloride under nitrogen at a temperature in the region of 20° C. After reacting for 24 hours at a temperature in the region of 20° C., the reaction mixture is poured onto 400 g of ice. The mixture is extracted three times with 300 ml of ethyl ether. The organic phases are combined, washed with 100 ml of saturated sodium carbonate solution and with 200 ml of distilled water, then dried over magnesium sulphate and evaporated. After purification of the resulting solid by flash chromatography on a silica column (eluent dichloromethane/ethyl acetate (98/2 by volume)), 20.4 g of 5-phthalimidomethylindan-1-one are obtained in the form of a beige solid ($^1$H NMR spectrum in d6-DMSO, T 300 K, δ in ppm: 2.61 (2H, m, COCH$_2$), 3.08 (2H, t, J=5 Hz, CH$_2$), 4.90 (2H, s, CH$_2$), 7.38 (1H, d, J=7 Hz, arom. CH), 7.51 (1H, s, arom. CH), 7.61 (1H, d, J=7 Hz, arom. CH), between 7.85 and 8.00 (4H, m, phthal. H)).

3-[3-(Phthalimidomethyl)phenyl]propanoic acid can be synthesized in the following way: 4.9 g of 10% palladium-on-charcoal are added to a solution of 48.7 g of 3-(phthalimidomethyl)cinnamic acid in 730 ml of dimethylformamide and 230 ml of absolute ethanol and the mixture is placed under hydrogen at a pressure in the region of 1 bar and at a temperature in the region of 20° C. After reacting for 4 hours, the reaction mixture is filtered on celite and the filtrate is evaporated under reduced pressure. 43.1 g of 3-[3-(phthalimidomethyl)phenyl]propanoic acid are thus obtained in the form of a white solid ($^1$H NMR spectrum in d6-DMSO, T=300 K, δ in ppm: 2.52 (2H, m, COCH$_2$), 2.80 (2H, t, J=7 Hz, CH$_2$), 4.77 (2H, s, NCH$_2$), between 7.10 and 7.35 (4H, m, arom. H), between 7.85 and 8.00 (4H, m, phthal. H), 12.20 (1H, s, COOH)). 3-(Phthalimidomethyl) cinnamic Acid can be prepared in the following way: 114.4 g of 1-bromo-3-(phthalimidomethyl)phenyl, 7.5 g of tri-o-tolylphosphine, 0.8 g of palladium acetate, 200 ml of tributylamine and then, dropwise, 30 ml of acrylic acid are introduced successively into a round-bottomed flask under a stream of nitrogen. The mixture is heated for 2 hours and 30 minutes at 110° C. During this period of time, an increase in the temperature of the reaction mixture, which reaches 140° C., followed by stabilization at 110° C., is observed. After returning to a temperature in the region of 20° C., 300 ml of dimethylformamide, 300 ml of methanol and 11 g of animal charcoal are added to the reaction mixture. The suspension is heated for 5 minutes at 80° C. and filtered on celite and the filtrate is evaporated under reduced pressure. The residue is taken up in 900 ml of methanol. The mixture is brought to reflux for 15 minutes, then cooled to a temperature in the region of 20° C. and filtered. 88.6 g of 3-(phthalimidomethyl)cinnamic acid are thus obtained in the form of a white solid ($^1$H NMR spectrum in d6-DMSO, T=300 K, δ in ppm: 4.80 (2H, s, NCH$_2$), 6.55 (1H, d, J=15 Hz, =CH), 7.4 (2H, m, arom. CH), 7.60 (1H, d, J=15 Hz, =CH), 7.65 (2H, m, arom. CH), between 7.85 and 8.00 (4H, m, phthal. H)). 1-Bromo-3-(phthalimidomethyl)phenyl can be obtained as follows: a solution of 150 g of 3-bromobenzyl bromide in 1.5 liter of dimethylformamide, to which 155.6 g of potassium phthalimide has been added, is heated for 16 hours at 60° C. After returning to a temperature in the region of 20° C., the reaction mixture is filtered on sintered glass and the filtrate is evaporated. The residue is taken up in 400 ml of methanol and the resulting suspension is stirred for 1 hour at a temperature in the region of 20° C. 163.9 g of 1-bromo-3-(phthalimidomethyl)phenyl are isolated by filtration in the form of a white solid ($^1$H NMR spectrum in d6-DMSO, T=300 K, δ in ppm: 4.80 (2H, s, NCH$_2$), between 7.25 and 7.35 (2H, m, arom. 2H), 7.49 (1H, m, arom. CH), 7.55 (1H, s, arom. CH), between 7.85 and 8.00 (4H, m, phthal. H)).

EXAMPLE 16

1.1 ml of triethylamine and then 0.52 ml of acetic anhydride are added to a suspension of 0.8 g of 8-aminomethyl-5H,10H-imidazo[1,2-a]indeno[1,2-e]pyrazin-4-one hydrochloride in 20 ml of dimethylformamide. After reacting for 18 hours at a temperature in the region of 20° C., the reaction mixture is filtered and the solid is washed successively with dimethylformamide, distilled water and acetone and then dried under reduced pressure (1 mbar) at 50° C. 0.81 g of N-[(4,5-dihydro-4-oxo-10H-imidazo[1,2-a]indeno[1,2-e]pyrazin-8-yl)methyl]acetamide is thus obtained in the form of a white solid melting above 260° C. (Analysis; % Calculated C: 65.30, H: 4.79, N: 19.04; % Found C: 65.3, H: 4.8, N: 18:7).

EXAMPLE 17

1.4 ml of triethylamine and 0.9 ml of phenylacetyl chloride are added to a suspension of 1 g of 8-aminomethyl-5H, 10H-imidazo[1,2-a]indeno[1,2-e]pyrazin-4-one hydrochloride in 40 ml of dimethylformamide. After reacting for 16 hours at a temperature in the region of 20° C., the reaction mixture is filtered and the filtrate is evaporated under reduced pressure. The residue is suspended in 50 ml of acetone. After filtration and drying under reduced pressure (1 mbar) at 60° C., 100 mg of N-[(4,5-dihydro-4-oxo-10H-imidazo[1,2-a]indeno[1,2-e]pyrazin-9-yl)methyl] phenylacetamide are obtained in the form of a beige solid melting above 260° C. ($^1$H NMR spectrum in d6-DMSO, T=300 K, δ in ppm: 3.51 (2H, s, CH$_2$-Ph), 3.97 (2H, s, CH$_2$), 4.35 (2H, d, J=4 Hz, NCH$_2$), between 7.20 and 7.40 (6H, m, arom. H), 7.43 (1H, s, arom. CH), 7.60 (1H, s, arom. CH), 7.78 (1H, d, J=7 Hz, arom. CH), 7.98 (1H, s, arom. CH), 8.63 (1H, broad t, NH), 12.3 (1H, s, NH)).

EXAMPLE 18

11.8 ml of 1N sodium hydroxide solution are added dropwise, at a temperature in the region of 20° C., to a suspension of 1.5 g of ethyl 9-ethoxycarbonylmethyl-4,5-dihydro-4-oxo-10H-imidazo[1,2-a]indeno[1,2-e]pyrazin-2-carboxylate in a mixture of 150 ml of dioxane and 40 ml of distilled water. The brown solution thus obtained is stirred for 4 hours at the same temperature. The precipitate formed is filtered and washed with dioxane and then with ethyl ether. The trisodium salt of 9-carboxymethyl-4,5-dihydro-4-oxo-10H-imidazo[1,2-a]indeno[1,2-e]pyrazin-2-carboxylic acid hydrate is thus obtained (Analysis C$_{16}$H$_8$N$_3$Na$_3$O$_5$; % Calculated C: 49.12, H: 2.06, N: 10.74, Na: 17.63; % Found (on a dry basis) C: 49.5, H: 2.1, N: 10.6, Na: 17.2). This salt is taken up in distilled water and the aqueous solution thus obtained is acidified using 0.5N hydrochloric acid. The new precipitate is filtered, washed with water and then with methanol and dried under reduced pressure (1 mm Hg; 0.13 kPa) at 45° C. to result in 0.91 g of 9-carboxymethyl-4,5-dihydro-4-oxo-10H-imidazo[1,2-a] indeno[1,2-e]pyrazin-2-carboxylic acid dihydrate in the form of a white powder, the melting point of which is greater than 260° C. (Analysis C16H15N3O7.0.35H2O; % Calculated C: 53.19, H: 4.18, N: 11.63, O: 31.00; % Found C: 53.2, H: 4.0, N: 11.4, O: 31.0); $^1$H NMR spectrum: 250 MHz, d6-DMSO, T=300 K, δ in ppm: 3.78 (2H, s, COCH$_2$), 4.03 (2H, s, CH$_2$), 7.28 (1H, d, J=7 Hz, arom. CH), 7.42 (1H, t, J=7 Hz, arom. CH), 7.85 (1H, d, J=7 Hz, arom. CH), 8.55 (1H, s, arom. CH), 12.5 (1H, s, NH)). The monohydrate (Analysis; % Calculated C: 55.98, H: 3.82, N: 12.24; % Found C: 55.2, H 3.6, N 12.0) is obtained by drying the dihydrate at 60° C. The disodium salt of 9-carboxymethyl-4,5-dihydro-4-oxo-10H-imidazo[1,2-a]indeno[1,2-e] pyrazine-2-carboxylic acid can also be obtained by treatment of the acid with 2 equivalents of 1N sodium hydroxide solution (Analysis; C16H9N3O5Na2.3H2O); % Calculated C: 52.04, H: 2.46, N: 11.38, Na: 12.45; % Found C: 51.7, H: 1.8, N: 11.4, Na: 12.6).

EXAMPLE 18A

Ethyl 9-ethoxycarbonylmethyl-4,5-dihydro-4-oxo-10H-imidazo[1,2-a]indeno[1,2-e]pyrazin-2-carboxylate can be obtained in the following way: 7.1 g of diethyl 1-(4-ethoxycarbonylmethyl-1-oxoindan-2-yl)imidazole-2,4-dicarboxylate and 83 g of ammonium acetate, in suspension in 140 ml of acetic acid, are heated at reflux for 3 hours. After cooling to a temperature in the region of 20° C., the insoluble material is filtered, washed with distilled water and then with acetone and dried. 4.7 g of the expected compound are obtained in the form of a light-grey solid, the melting point of which is greater than 260° C. ($^1$H NMR spectrum: 200 MHz, d6-DMSO, T=300 K, δ in ppm: 1.21 (3H, t, J=6 Hz, CH$_3$), 1.37 (3H, t, J=6 Hz, CH$_3$), 3.82 (2H, s, COCH$_2$), 4.01 (2H, s, CH$_2$), 4.37 (2H, q, J=6 Hz, OCH$_2$), 7.28 (1H, d, J=7 Hz, arom. CH), 7.42 (1H, t, J=7 Hz, arom. CH), 7.83 (1H, d, J=7 Hz, arom. CH), 8.06 (1H, s, arom. CH)).

Diethyl 1-(4-ethoxycarbonylmethyl-1-oxoindan-2-yl) imidazole-2,4-dicarboxylate can be prepared in the following way: a solution of 9.8 g of the ethyl ester of (2-bromo-1-oxoindan-4-yl)acetic acid in 100 ml of acetone is added dropwise to a suspension of 6.99 g of diethyl imidazole-2,4-dicarboxylate and 22 g of potassium carbonate in 100 ml of acetone at reflux. The reaction mixture is heated at reflux for 3 hours and 30 minutes, then cooled to a temperature in the region of 20° C. and the insoluble material is filtered and washed with acetone. The filtrate is then concentrated to dryness under reduced pressure and the crude product thus obtained purified by flash chromatography on a silica column, using an ethyl acetate/dichloromethane (20/80 by volume) mixture as eluent. 7.1 g of the expected product are obtained in the form of a brown oil ($^1$H NMR spectrum: 250 MHz, d6-DMSO, T=300 K, δ in ppm: 1.18 (3H, t, J=6 Hz, CH$_3$), 1.20 (3H, t, J=6 Hz, CH$_3$), 1.35 (3H, t, J=6 Hz, CH$_3$), 3.38 and 3.80 (each 1H, respectively dd, J=6 and 16 Hz, and dd, J=8 and 16 Hz, CH$_2$), 3.88 (2H, s, COCH$_2$), 4.12 (4H, m, 2 times OCH$_2$), 4.32 (2H, q, J=6 Hz, OCH$_2$), 5.91 (1H, t, J=6 and 8 Hz, CH), 7.55 (1H, t, J=7 Hz, arom. CH), 7.73 (2H, d, J=7 Hz, arom. CH), 8.37 (1H, s, CH)).

EXAMPLE 19

A mixture of 0.9 g of 4-benzylcarbamoyl-2-(2-ethoxycarbonylimidazolyl)-1-indanone, 30 ml of acetic acid and 17.2 g of ammonium acetate is heated at reflux for 1 hour and 30 minutes. 30 ml of distilled water are added to the reaction mixture and the reaction mixture is cooled in a bath of ice-cold water for 30 minutes. The precipitate is filtered and washed with distilled water (3×10 ml), with ethanol (10 ml) and finally with acetone (3×10 ml). After drying at 50° C. under vacuum (1 mm Hg; 0.13 kPa), 0.63 g of N-benzyl-(4,5-dihydro-4-oxo-10H-imidazo[1,2-a] indeno[1,2-e]pyrazin-9-yl)carboxamide is obtained in the form of a beige solid melting above 260° C. (Analysis; % Calculated C: 70.77, H: 4.53, N: 15.72, O: 8.98; % Found C: 70.8, H: 4.5, O: 9.0).

4-Benzylcarbamoyl-2-(ethoxycarbonylimidazolyl)-1-indanone can be prepared in the following way: a mixture of 0.5 g of 4-benzylcarbamoyl-2-bromo-1-indanone, 0.37 g of 2-ethoxycarbonylimidazole and 10 ml of toluene is heated at reflux for 12 hours. The reaction mixture is concentrated on a rotary evaporator. Dichloromethane is added to the evaporation residue, filtration is carried out and the filtrate is washed with distilled water, dried over sodium sulphate and evaporated on a rotary evaporator. The brown oil obtained (0.26 g) is purified by chromatography on a silica column (diameter: 1.5 cm, height: 30 cm), elution being carried out with a dichloromethane/methanol (95/5 by volume) mixture. The foamy product obtained is triturated with 5 ml of ethyl acetate, filtered and the solid is washed-with ethyl acetate (2 × 5 ml) and dried at 50° C. under vacuum (1 mm Hg; 0.13 kPa). 0.07 g of 4-benzylcarbamoyl-2-(2-ethoxycarbonylimidazolyl)-1-indanone is obtained in the form of an orange solid melting at 218° C.

4-Benzylcarbamoyl-2-bromo-1-indanone can be prepared in the following way: a solution of 2.72 g of bromine in 10 ml of acetic acid is added dropwise to a stirred mixture of 4.5 g of 4-benzylcarbamoyl-1-indanone, 40 ml of acetic acid and 0.55 ml of concentrated hydrobromic acid, the temperature of the reaction mixture being maintained at approximately 16° C. Stirring is continued for 30 minutes at approximately 16° C. and then for 2 hours at a temperature in the region of 20° C. The reaction mixture is then treated with 100 ml of water and extracted with ethyl acetate. The organic phase is washed with distilled water, dried over sodium sulphate and evaporated on a rotary evaporator. After drying at 65° C. under 10 mm Hg, 5.7 g of 4-benzylcarbamoyl-2-bromo-1-indanone are obtained in the form of a yellow oil which is not slow in crystallizing, which oil is used as is in the subsequent syntheses.

4-Benzylcarbamoyl-1-indanone can be prepared in the following way: a solution of 3.34 ml of benzylamine in 30 ml of dimethylformamide is added dropwise, under a nitrogen blanket, to a stirred solution of 5 g of 1-oxoindane-4-carboxylic acid in 270 ml of dimethylformamide. Stirring is continued for 10 minutes before addition of 4 g of 1-hydroxybenzotriazole and 5.68 g of 1-(3-dimethylaminopropyl)-3-ethylcarbodiimide hydrochloride. Stirring is maintained overnight and the reaction mixture is then treated with 250 ml of water and extracted with ethyl acetate (3×250 ml). The organic phase is washed with distilled water (2×250 ml), dried over sodium sulphate and evaporated on a rotary evaporator. The evaporation residue is purified by chromatography on a silica column (diameter: 2.5 cm, height: 50 cm), elution being carried out with a cyclohexane/ethyl acetate (50/50 by volume) mixture. 4.5 g of 4-benzylcarbamoyl-1-indanone are obtained in the form of an orange-yellow solid melting at 124° C.

1-Oxoindane-4-carboxylic acid can be prepared in the following way: 1500 ml of toluene and then, portionwise, 90 g of 3-(1-oxoindan-4-yl)acrylic acid are added to a solution, cooled in a bath of ice-cold water, consisting of 190.3 g of potassium permanganate in 2000 ml of distilled water and 20 g of tetrabutylammonium bromide. The reaction mixture is stirred overnight at a temperature in the region of 20° C. and then 200 ml of water and sodium bisulphite are added until the reaction mixture has decoloured. After acidification to pH 1 with 6N hydrochloric acid, the suspension obtained is filtered and the filtrate is separated by settling. The aqueous phase is extracted with ethyl acetate and the organic phase obtained is added to the toluene phase. After evaporation on a rotary evaporator, 35 g of 1-oxoindane-4-carboxylic acid are obtained in the form of an orange solid melting at 215° C.

3-(1-Oxoindan-4-yl)acrylic acid can be prepared in the following way: 20.26 g of acrylic acid are added to a mixture of 59.1 g of 4-bromo-1-indanone, 107.9 g of tributylamine, 6.1 g of tri-o-tolylphosphine and 0.63 g of palladium acetate and the reaction mixture is heated at 100° C. for 2 hours. The reaction mixture is cooled to a temperature in the region of 20° C. and treated with 400 ml of water and 50 g of sodium hydrogencarbonate. The mixture is then filtered and the aqueous phase is washed with ethyl ether (2×250 ml) and acidified with 100 ml of 6N hydrochloric acid. The precipitate formed is filtered, washed with 1N hydrochloric acid and dried, first in air and then at 50° C. under vacuum (1 mm Hg; 0.13 kPa). 48.7 g of 3-(1-oxoindan-4-yl)acrylic acid are obtained in the form of a pale-yellow solid melting at 190° C.

4-Bromo-1-indanone can be prepared according to the process described by M. Adamczyk et al., J. Org. Chem., 49(22), 4226 (1984).

EXAMPLE 20

The preparation is carried out as in Example 19 but from 0.9 g of 4-phenylcarbamoyl-2-(2-ethoxycarbonylimidazolyl)-1-indanone, 30 ml of acetic acid and 17.8 g of ammonium acetate. 0.55 g of N-phenyl-4,5-dihydro-4-oxo-10H-imidazo[1,2-a]indeno[1,2-e]pyrazine-9-carboxamide is obtained in the form of a pale-pink solid melting above 260° C. (Analysis; % Calculated C: 70.17, H: 4.12, N: 16.36, O: 9.35; % Found C: 70.1, H: 3.8, N: 16.2).

4-Phenylcarbamoyl-2-(2-ethoxycarbonylimidazolyl)-1-indanone can be prepared in the following way: the preparation is carried out as in Example 19 for 4-benzylcarbamoyl-2-(2-ethoxycarbonylimidazolyl)-1-indanone but from 3 g of 4-phenylcarbamoyl-2-bromo-1-indanone, 80 ml of toluene and 2.55 g of 2-ethoxycarbonylimidazole. The crude product is purified with the help of two chromatographic purifications on a silica column (diameter: 2.5 cm, height: 30 cm), elution being carried out with ethyl acetate. 0.81 g of 9-phenylcarbamoyl-2-(2-ethoxycarbonylimidazolyl)-1-indanone is obtained in the form of a pale-yellow solid melting at 246° C.

4-Phenylcarbamoyl-2-bromo-1-indanone can be prepared in the following way: the preparation is carried out as in Example 19 for 4-benzylcarbamoyl-2-bromo-1 -indanone but from 4.9 g of 4-phenylcarbamoyl-1-indanone, 60 ml of acetic acid, 0.6 ml of concentrated hydrobromic acid and 2.97 g of bromine. 4 g of 4-phenylcarbamoyl-2-bromo-1-indanone are obtained in the form of a pale-yellow solid melting at 212° C.

4-Phenylcarbamoyl-1-indanone can be prepared in the following way: the preparation is carried out as in Example 19 for 4-benzylcarbamoyl-1-indanone but from 5 g of 1-oxoindane-4-carboxylic acid, 300 ml of dimethylformamide, 2.85 g of aniline, 4 g of 1-hydroxybenzotriazole and 5.68 g of 1-(3-dimethylaminopropyl)-3-ethylcarbodiimide hydrochloride. 4.9 g 4-phenylcarbamoyl-1-indanone are obtained in the form of a brown solid melting at 150° C.

EXAMPLE 21

The preparation is carried out as in Example 19 but from 3 g of 4-(methoxycarbonylmethylcarbamoyl)-2-(2-ethoxycarbonylimidazolyl)-1-indanone, 100 ml of acetic acid and 60 g of ammonium acetate. The precipitate, after washing with water, is dried in air and crystallized from 48 ml of dimethylformamide. The crystals are washed with isopropyl ether and dried at 60° C. under vacuum (1 mm Hg; 0.13 kPa). 0.96 g of methyl N-[(4,5-dihydro-4-oxo-10H-imidazo[1,2-a]indeno[1,2-e]pyrazin-9-yl)carbonyl] glycinate is obtained in the form of a pink solid melting above 260° C. (Analysis; % Calculated C: 60.35, H: 4.17, N: 16.56, O: 18.92; % Found H: 4.2, N: 16.2, O: 18.3; ($^1$H NMR spectrum: 250 MHz, (CD3)2SO, δ in ppm: 3.7 (s, 3H, methyl), 4.10 (d, J=6 Hz, 2H, CH$_2$N), 4.30 (s, 1H, CH$_2$), 7.52 (t, J=7 Hz, 2H, aromatic H); 7.55 (s, 1H, heterocyclic H), 7.70 (d, J=7 Hz, 1H, aromatic H), 8.05 (d, J=7 Hz, 1H, aromatic H), 8.10 (s, 1H, heterocyclic H), 9.05 (t, J=6 Hz, 1H, CONH), 12.45 (bs, 1H, NH)).

4-(Methoxycarbonylmethylcarbamoyl)-2-(2-ethoxycarbonylimidazolyl)-1-indanone can be prepared in the following way: the preparation is carried out as in Example 19 for 4-benzylcarbamoyl-2-(2-ethoxycarbonylimidazolyl)-1-indanone but from 10.2 g of 4-(methoxycarbonylmethylcarbamoyl)-2-bromo-1-indanone, 200 ml of toluene and 7 g of 2-ethoxycarbonylimidazole. The crude product, dissolved in a mixture of methanol and dichloromethane, is purified by chromatography on a silica column (diameter: 4.5 cm, height: 47 cm), elution being carried out with an ethyl acetate/dichloromethane (80/20 by volume) mixture. 3 g of 4-(methoxycarbonylmethylcarbamoyl)-2-(2-ethoxycarbonylimidazolyl)-1-indanone are obtained in the form of an orange solid melting at 143° C.

4-(Methoxycarbonylmethylcarbamoyl)-2-bromo-1-indanone can be prepared in the following way: the preparation is carried out as in Example 19 for 4-benzylcarbamoyl-2-bromo-1-indanone but from 9.04 g of 4-(methoxycarbonylmethylcarbamoyl)-1-indanone, 120 ml of acetic acid, 1.7 ml of concentrated hydrobromic acid and 6.6 g of bromine. 11 g of 4-(methoxycarbonylmethylcarbamoyl)-2-bromo-1-indanone are obtained in the form of an orange oil which then crystallizes and is used as is in the subsequent syntheses.

4-(Methoxycarbonylmethylcarbamoyl)-1-indanone can be prepared in the following way: the preparation is carried out as in Example 19 for 4-benzylcarbamoyl-1-indanone but from 10 g of 1-oxoindane-4-carboxylic acid, 400 ml of dichloromethane, 7.4 g of methyl glycinate hydrochloride, 6 g of triethylamine, 7.9 g of 1-hydroxybenzotriazole and 11.25 g of 1-(3-dimethylaminopropyl)-3-ethylcarbodiimide hydrochloride. The crude product is purified by chromatography on a silica column (diameter: 2.5 cm, height: 38 cm), elution being carried out with a dichloromethane/ethyl acetate (60/40 by volume) mixture. 8.7 g of 4-(methoxycarbonylmethylcarbamoyl)-1-indanone are obtained in the form of a pale-yellow solid melting at 122° C.

EXAMPLE 22

A mixture of 1 g 9-(methoxycarbonylmethylcarbamoyl)-5H,10H-imidazo[1,2-a]indeno[1,2-e]pyrazin-4-one, 50 ml of dioxane and 15 ml of concentrated hydrochloric acid is heated at reflux for 24 hours. The reaction mixture is concentrated on a rotary evaporator, ethyl ether is added to the evaporation residue and filtration is carried out. The solid obtained is triturated in 20 ml of distilled water, filtered, washed with distilled water (20 ml) and then with ethyl ether and dried at 60° C. under vacuum (1 mm Hg; 0.13 kPa). 0.8 g of N-[(4,5-dihydro-4-oxo-10H-imidazo[1,2-a]indeno[1,2-e]pyrazin-9-yl)carbonyl]glycine is obtained in the form of a yellow solid containing 0.66 mol of hydrochloric acid and melting above 260° C (Analysis; % Calculated C: 55.13, H: 3.66, Cl: 6.78, N: 16.07, O: 18.36; % Found C: 55.1, H: 3.6, Cl: 6.2, N: 15.8, O: 18.3).

EXAMPLE 23

The preparation is carried out as in Example 19 but from 0.9 g of 5-phenylcarbamoyl-2-(2-ethoxycarbonylimidazolyl)-1-indanone, 32 ml of acetic acid and 17.7 g of ammonium acetate. 0.5 g of N-phenyl-(4,5-dihydro-4-oxo-10H-imidazo [1,2-a]indeno [1,2-e]pyrazin-8-yl) carboxamide is obtained in the form of a brown solid melting above 260° C. (Analysis; % Calculated C: 70.16, H: 4.12, N: 16.37, O: 9.35; % Found C: 70.1, H: 3.6, N: 15.8).

5-Phenylcarbamoyl-2-(2-ethoxycarbonylimidazolyl)-1-indanone can be prepared in the following way: the preparation is carried out as in Example 19 for 4-benzylcarbamoyl-2-(2-ethoxycarbonylimidazolyl)-1-indanone but from 3.65 g of 5-phenylcarbamoyl-2-bromo-1-indanone, 73 ml of toluene and 3.1 g of 2-ethoxycarbonylimidazole. The crude product is purified by chromatography on a silica column, elution being carried out first with a dichloromethane/methanol (99.5/0.5by volume) mixture and then with a dichloromethane/methanol (98/2 by volume) mixture. 0.9 g of 5-phenylcarbamoyl-2-(2-ethoxycarbonylimidazolyl)-1-indanone is obtained in the form of a brown solid melting at 122° C.

5-Phenylcarbamoyl-2-bromo-1-indanone can be prepared in the following way: the preparation is carried out as in Example 19 for 4-benzylcarbamoyl-2-bromo-1-indanone but from 3.1 g of 5-phenylcarbamoyl-1-indanone, 37 ml of acetic acid, 0.4 ml of concentrated hydrobromic acid and 1.96 g of bromine. 3.7 g of 5-phenylcarbamoyl-2-bromo-1-indanone are obtained in the form of a greyish-green solid melting at 144° C.

5-Phenylcarbamoyl-1-indanone can be prepared in the following way: the preparation is carried out as in Example 19 for 4-benzylcarbamoyl-1-indanone but from 4.4 g of 1-oxoindane-5-carboxylic acid, 2.86 g of aniline, 100 ml of dichloromethane, 3.5 g of 1-hydroxybenzotriazole and 5 g of 1-(3-dimethylaminopropyl) -3-ethylcarbodiimide hydrochloride. The crude product is purified by chromatography on a silica column, elution being carried out with a dichloromethane/methanol (99/1 by volume) mixture. 3.1 g of 5-phenylcarbamoyl-1-indanone are obtained in the form of a brown solid melting at 174° C.

1-Oxoindane-5-carboxylic acid can be prepared in the following way: the preparation is carried out as in Example 19 for 1-oxoindane-4-carboxylic acid but from 22.3 g of 3-(1-oxoindan-5-yl)acrylic acid, 560 ml of distilled water, 370 ml of toluene, 4.95 g of tetrabutylammonium bromide and 47.4 g of potassium permanganate. 14.4 g of 1-oxoindane-5-carboxylic acid are obtained in the form of a cream-coloured solid melting at 270° C.

3-(1-Oxoindan-5-yl)acrylic acid can be prepared in the following way: the preparation is carried out as in Example 19 for 3-(1-oxoindan-4-yl)acrylic acid but from 106.9 g of 5-bromo-1-indanone, 250 ml of tributylamine, 10.9 g of tri-o-tolylphosphine, 1.1 g of palladium acetate and 36.6 g of acrylic acid. The precipitate formed by acidification with 6N hydrochloric acid is purified by chromatography on a silica column, elution being carried out with a mixture of dichloromethane and methanol (97.5/2.5 by volume). 22.3 g of 3-(1-oxoindan-5-yl)acrylic acid are obtained in the form of an ochre solid melting at 234° C.

5-Bromo-1-indanone can be prepared according to the process described by J. P. Quèmre and E. Maréchal, Bull. Soc. Chim. Fr., (8), 2983 (1971).

EXAMPLE 24

The preparation is carried out as in Example 19 but from 0.8 g of 5-benzylcarbamoyl-2-(2-ethoxycarbonylimidazolyl)-1-indanone, 28 ml of acetic acid and 15.2 g of ammonium acetate. 0.5 g of N-benzyl-(4,5-dihydro-4-oxo-10H-imidazo[1,2-a]indeno[1,2-e]pyrazin-8-yl)carboxamide is obtained in the form of a grey solid melting above 260° C. (Analysis; % Calculated C: 70.77, H: 4.53, N: 15.72, O: 8.98; % Found C: 70.8, H: 4.8, O: 8.6).

5-Benzylcarbamoyl-2-(2-ethoxycarbonylimidazolyl)-1-indanone can be prepared in the following way: the preparation is carried out as in Example 19 for 4-benzylcarbamoyl-2-(2-ethoxycarbonylimidazolyl)-1-indanone but from 4.1 g of 5-benzylcarbamoyl-2-bromo-1-indanone, 82 ml of toluene and 3.3 g of 2-ethoxycarbonylimidazole. The crude product is purified by chromatography on a silica column, elution being carried out with a dichloromethane/ethyl acetate (50/50 by volume) mixture. 0.9 g of 5-benzylcarbamoyl-2-(2-ethoxycarbonylimidazolyl)-1-indanone is obtained in the form of an ochre solid melting at 72° C.

5-Benzylcarbamoyl-2-bromo-1-indanone can be prepared in the following way: the preparation is carried out as in Example 19 for 4-benzylcarbamoyl-2-bromo-1-indanone but from 3.9 g of 5-benzylcarbamoyl-1-indanone, 45 ml of acetic acid, 0.47 ml of concentrated hydrobromic acid and 2.35 g of bromine. 5.1 g of 5-benzylcarbamoyl-2-bromo-1-indanone are obtained in the form of an orange-coloured pasty mass used as is in the subsequent syntheses.

5-Benzylcarbamoyl-1-indanone can be prepared in the following way: the preparation is carried out as in Example 19 for 4-benzylcarbamoyl-1-indanone but from 4.4 g of 1-oxoindan-5-carboxylic acid, 88 ml of dimethylformamide, 3 ml of benzylamine, 3.5 g of 1-hydroxybenzotriazole and 5 g of 1-(3-dimethylaminopropyl)-3-ethylcarbodiimide hydrochloride. The crude product is purified by chromatography on a silica column, elution being carried out with a dichloromethane/methanol (99/1 by volume) mixture. 3.9 g of 5-benzylcarbamoyl-1-indanone are obtained in the form of a yellow solid melting at 133° C.

EXAMPLE 25

A mixture of 850 mg of ethyl 8-(N-ethylaminocarbonylmethyl)-4,5-dihydro-4-oxo-10H-imidazo[1,2-a]indeno[1,2-e]pyrazin-2-carboxylate, 10 ml of dioxane, 40 ml of distilled water and 5.8 ml of 1N sodium hydroxide solution is stirred under a stream of argon at a temperature in the region of 20° C overnight. The reaction mixture is cooled to a temperature in the region of 0° C. and neutralized with 5.8 ml of 1N hydrochloric acid. The precipitate obtained is filtered, washed with distilled water a number of times and dried in an oven. 695 mg of 8-(N-ethylaminocarbonylmethyl)-4,5-dihydro-4-oxo-10H-imidazo[1,2-a]indeno[1,2-e]pyrazin-2-carboxylic acid are obtained in the form of a brown solid melting above 300° C. ($^1$H NMR spectrum in d6-DMSO, T=300 K, δ in ppm (300 MHz): 1.05 (3H, t, J=6 Hz, $CH_3$), 3.10 (2H, m, $NCH_2$), 3.47 (2H, s, $CH_2CO$), 4.02 (2H, s, $CH_2$), 7.30 (1H, d, J=8 Hz, arom. CH), 7.48 (1H, 8, arom. CH), 7.82 (1H, d, J=8 Hz, arom. CH), 8.08 (1H, t, J=5 Hz, NH), 8.52 (1H, s, imidazole H)).

EXAMPLE 26

A mixture of 3.9 g of diethyl 1-[5-(N-ethylaminocarbonylmethyl)-1-oxoindan-2-yl]imidazole-2,4-dicarboxylate, 33.4 g of ammonium acetate and 200 ml of acetic acid is heated at reflux for 3 hours. The reaction mixture is evaporated on a rotary evaporator, 250 ml of distilled water are added to the evaporation residue and the residue is filtered. The solid obtained is washed with distilled water a number of times and dried in an oven. 2.2 g of ethyl 8-(N-ethylaminocarbonylmethyl)-4,5-dihydro-4-oxo-10H-imidazo[1,2-a]indeno[1,2-e]pyrazin-2-carboxylate are obtained in the form of a light-brown solid melting above 300° C. ($^1$H NMR spectrum in d6-DMSO, T=300 K, δ in ppm (300 MHz): 1.05 (3H, t, J=6 Hz, $CH_3$), 1.40 (3H, t, J=6 Hz, $CH_3$), 3.12 (2H, m, $NCH_2$), 3.48 (2H, s, $CH_2CO$), 4.05 (2H, s, $CH_2$), 4.40 (2H, q, J=6 Hz, $CH_2O$), 7.32 (1H, d, J=8 Hz,-arom. CH), 7.42 (1H, 8, arom. CH), 7.83 (1H, d, J=8 Hz, arom. CH), 8.10 (1H, t, J=5 Hz, NH), 8.60 (1H, s, imidazole H)).

Diethyl 1-[5-(N-ethylaminocarbonylmethyl)-1-oxoindan-2-yl]imidazole-2,4-dicarboxylate can be prepared in the following way: a mixture of 1.84 g of diethyl imidazole-2,4-dicarboxylate, 150 ml of dimethylformamide and 3.6 g of potassium carbonate is heated for 2 hours at a temperature in the region of 85° C. The temperature of the reaction mixture is allowed to return to approximately 20° C. and a solution of 3.3 g of 2-bromo-5-(N-ethylaminocarbonylmethyl)indan-1-one in 50 ml of dimethylformamide is added with stirring. Stirring is continued overnight. The reaction mixture is evaporated on a rotary evaporator, 200 ml of distilled water are added to the evaporation residue and extraction is carried out with 5×200 ml of ethyl acetate. The organic phase is dried over magnesium sulphate, filtered and evaporated on a rotary evaporator. The residue obtained is purified by chromatography on a silica column, elution being carried out first with ethyl acetate and then with an ethyl acetate/methanol (95/5 by volume) mixture. 3.9 g of diethyl 1-[5-(N-ethylaminocarbonylmethyl)-1-oxoindan-2-yl]imidazole-2,4-dicarboxylate are obtained in the form of a white solid ($^1$H NMR spectrum in d6-DMSO, T=300 K, δ in ppm (300 MHz): 1.05 (3H, t, J=6 Hz, CH$_3$), 1.18 (3H, t, J=6 Hz, CH$_3$), 1.32 (3H, t, J=6 Hz, CH$_3$), 3.10 (2H, m, NCH$_2$), 3.43 and 3.72 (each 1H, respectively dd, J=5 and 13 Hz, and dd, J=7 and 13 Hz, CH$_2$), 3.55 (2H, s, COCH$_2$), 4.15 (2H, q, J=6 Hz, CH$_2$O), 4.30 (2H, q, J=6 Hz, CH$_2$O), 5.88 (1H, dd, J=7 and 5 Hz, NCH), 7.42 (1H, d, J=8 Hz, arom. CH), 7.50 (1H, s, arom. CH), 7.70 (1H, d, J=8 Hz, arom. CH), 8.20 (1H, t, J=5 Hz, NH), 8.30 (1H, s, imidazole H)).

2-Bromo-5-(N-ethylaminocarbonylmethyl)indan-1-one can be prepared in the following way: a solution of 3.2 g of 5-(N-ethylaminocarbonylmethyl)indan-1-one in 237 ml of dichloromethane and 183 ml of ethanol is cooled under an argon atmosphere to a temperature of between 0 and 3° C. and a solution of 0.75 ml of bromine in 36 ml of dichloromethane is added dropwise with stirring, the temperature of the reaction mixture being maintained below 5° C. Stirring is continued for 90 minutes at a temperature in the region of 20° C. and the reaction mixture is then evaporated on a rotary evaporator. The evaporation residue (7.3 g) is chromatographed on a silica column, elution being carried out first with ethyl acetate and then with an ethyl acetate/methanol (95/5 by volume) mixture. 3.3 g of 2-bromo-5-(N-ethylaminocarbonylmethyl)indan-1-one are obtained in the form of a white solid [Rf=0.64, silica thin layer chromatography, eluent: ethyl acetate/methanol (95/5 by volume)].

5-(N-Ethylaminocarbonylmethyl)indan-1-one can be prepared in the following way: a solution of 3 g of (1-oxoindan-5-yl)acetic acid in 75 ml of tetrahydrofuran is cooled, under a stream of argon, to a temperature in the region of 0° C. and 3.84 g of carbonyldiimidazole are added with stirring. Stirring is continued at a temperature of 20° C. for one hour and the reaction mixture is then cooled to a temperature in the region of −10° C. and 10.3 ml of triethylamine are added. The temperature of the mixture is allowed to return to the region of 20° C. and stirring is continued for 2 hours. The reaction mixture is concentrated on a rotary evaporator and 150 ml of dichloromethane are added. The organic phase is washed with 75 ml of distilled water, dried over magnesium sulphate, filtered and evaporated on a rotary evaporator. The evaporation residue (4.1 g) is purified by chromatography on a silica column, elution being carried out first with dichloromethane and then with a dichloromethane/methanol (96/4 by volume) mixture. 3.3 g of 5-(N-ethylaminocarbonylmethyl)indan-1-one are obtained in the form of a pale-pink solid (Rf=0.50, silica thin layer chromatography, eluent: ethyl acetate/methanol (95/5 by volume); $^1$H NMR spectrum in d6-DMSO, T=300 K, δ in ppm (300 MHz): 1.03 (3H, t, J=6 Hz, CH$_3$), 2.62 (2H, t, J=6 Hz, CH$_2$CO), between 2.90 and 3.15 (4H, m, CH$_2$ and NCH$_2$), 3.50 (2H, s, CH$_2$CO), 7.30 (1H, d, J=8 Hz, arom. CH), 7.45 (1H, s, arom. CH), 7.60 (1H, d, J=8 Hz, arom. CH), 8.12 (1H, t, J=5 Hz, NH)).

EXAMPLE 27

The preparation is carried out as in Example 25 but from 0.3 g of ethyl 8-(N,N-dimethylaminocarbonylmethyl)-4,5-dihydro-4-oxo-10H-imidazo[1,2-a]indeno[1,2-e]pyrazin-2-carboxylate, 15 ml of dioxane, 15 ml of water and 2.3 ml of 1N sodium hydroxide solution. 0.2 g of 8-(N,N-dimethylaminocarbonylmethyl)-4,5-dihydro-4-oxo-10H-imidazo[1,2-a]indeno[1,2-e]pyrazin-2-carboxylic acid is obtained in the form of an ochre solid melting above 260° C. (Analysis C$_{18}$H$_{16}$N$_4$O$_4$; % Calculated C: 61.36, H: 4.58, N: 15.90, O: 18.16; % Found C: 61.1, H: 4.5, N: 15.6, O: 18.0).

Ethyl 8-(N,N-dimethylaminocarbonylmethyl)-4,5-dihydro-4-oxo-10H-imidazo[1,2-a]indeno[1,2-e]pyrazine-2-carboxylate can be prepared in the following way: the preparation is carried out as in Example 26 but from 0.5 g of diethyl 1-[5-(N,N-dimethylaminocarbonylmethyl)-1-oxoindan-2-yl]imidazole-2,4-dicarboxylate, 4.7 g of ammonium acetate and 25 ml of acetic acid. 0.3 g of ethyl 8-(N,N-dimethylaminocarbonylmethyl)-4,5-dihydro-4-oxo-10H-imidazo[1,2-a]indeno[1,2-e]pyrazine-2-carboxylate is obtained in the form of a brown solid melting above 260° C. which is used as is in the subsequent syntheses.

Diethyl 1-[5-(N,N-dimethylaminocarbonylmethyl)-1-oxoindan-2-yl]imidazole-2,4-dicarboxylate can be prepared in the following way: the preparation is carried out as in Example 26 for the preparation of diethyl 1-[5-(N-ethylaminocarbonylmethyl)-1-oxoindan-2-yl]imidazole-2,4-dicarboxylate but from 1.2 g of diethyl imidazole-2,4-dicarboxylate, 150 ml of dimethylformamide, 2.37 g of potassium carbonate and 2.2 g of 2-bromo-5-(N,N-dimethylaminocarbonylmethyl)indan-1-one. The crude product is purified by chromatography on a silica column, elution being carried out with an ethyl acetate/methanol (90/10 by volume) mixture. 0.56 g of diethyl 1-[5-(N,N-dimethylaminocarbonylmethyl)-1-oxoindan-2-yl)imidazole-2,4-dicarboxylate is obtained in the form of cream-coloured foam (Rf=0.36, silica thin layer chromatography, eluent: ethyl acetate/methanol (90/10 by volume)).

2-Bromo-5-(N,N-dimethylaminocarbonylmethyl)indan-1-one can be prepared in the following way: the preparation is carried out as in Example 26 for the preparation of 2-bromo-5-(N-ethylaminocarbonylmethyl)indan-1-one but from 2.2 g of 5-(N,N-dimethylaminocarbonylmethyl)indan-1-one, 185 ml of dichloromethane, 60 ml of ethanol and 0.5 ml of bromine. The crude product is chromatographed on a silica column, elution being carried out with a mixture of ethyl acetate and methanol (90/10 by volume). 2.2 g of 2-bromo-5-(N,N-dimethylaminocarbonylmethyl)indan-1-one are obtained in the form of an orange pasty solid (Rf=0.53, silica thin layer chromatography, eluent: ethyl acetate/methanol (90/10 by volume)).

5-(N,N-Dimethylaminocarbonylmethyl)indan-1-one can be prepared in the following way: 0.86 ml of oxalyl chloride is added with stirring to a mixture of 1.9 g of (1-oxoindan-5-yl)acetic acid, 50 ml of dichloromethane and 5 drops of dimethylformamide and stirring is continued for 3 hours at a temperature in the region of 20° C. 1.4 ml of triethylamine are then added, followed by 7 ml of a 2M solution of dimethylamine in toluene. Stirring is continued overnight. The reaction mixture is treated with 100 ml of dichloromethane and 30 ml of distilled water. The organic phase is dried over magnesium sulphate, filtered and evaporated on a rotary evaporator. 2.2 g of 5-(N,N-dimethylaminocarbonylmethyl)indan-1-one are obtained in the form of a brown pasty solid (Rf=0.44, silica thin layer chromatography, eluent: ethyl acetate/methanol (90/10 by volume)).

EXAMPLE 28

6.5 ml of hydrochloric acid (6N) are added to a suspension of 0.65 g of ethyl 9-benzylcarbamoyl-4,5-dihydro-4-oxo-10H-imidazo[1,2-a]indeno[1,2-e]pyrazin-2-carboxylate in 26 ml of dioxane and the reaction mixture is brought to a temperature in the region of 100° C. for 7 hours. After cooling and maintaining stirring for one hour at a temperature in the region of 20° C., the precipitate thus obtained is filtered on sintered glass, washed with 2×10 ml of dioxane and then dried at 60° C. under reduced pressure. Recrystallization from 60 ml of a dimethylformamide/water (2/1 by volume) mixture of the solid obtained results, after drying at 60° C. under reduced pressure, in 0.4 g of 9-benzylcarbamoyl-4,5-dihydro-4-oxo-10H-imidazo[1,2-a]indeno[1,2-e]pyrazin-2-carboxylic acid in the form of a white solid, the melting point of which is greater than 260° C. (Analysis $C_{22}H_{16}N_4O_4.1.82H_2O.0.57C_3H_7NO$; % Calculated: C: 66.00, H: 4.03, N: 13.99, O: 15.98; % Found: C: 59.8, H: 4.0, N: 13.9).

Ethyl 9-benzylcarbamoyl-4,5-dihydro-4-oxo-10H-imidazo[1,2-a]indeno[1,2-e]pyrazine-2-carboxylate can be prepared in the following way: 0.75 g of diethyl 1-(4-benzylcarbamoyl-1-oxoindan-2-yl)imidazole-2,4-dicarboxylate and 6 g of ammonium acetate in suspension in 20 ml of acetic acid are heated at reflux for one hour. After cooling to a temperature in the region of 20° C., 20 ml of water are added to the reaction mixture which is kept stirring for 30 minutes and the insoluble material formed is filtered on sintered glass, washed with water and then dried under reduced pressure at 60° C. 0.65 g of ethyl 9-benzylcarbamoyl-4,5-dihydro-4-oxo-10H-imidazo[1,2-a]indeno[1,2-e]pyrazine-2-carboxylate is thus obtained in the form of a grey solid, the melting point of which is greater than 260° C., which is used as is in the subsequent syntheses.

Diethyl 1-(4-benzylcarbamoyl-1-oxoindan-2-yl)imidazole-2,4-dicarboxylate can be prepared in the following way: a solution of 0.5 g of 4-benzylcarbamoyl-2-bromo-1-indanone in 8 ml of acetone is added dropwise to a suspension of 0.31 g of diethyl imidazole-2,4-dicarboxylate and 1 g of potassium carbonate in 7 ml of acetone at reflux and reflux is maintained for 15 minutes. After cooling the reaction mixture to a temperature in the region of 20° C., the insoluble material is filtered on sintered glass and washed with acetone. The filtrate is concentrated to dryness under reduced pressure and the crude product thus obtained is purified by flash chromatography on a silica column, using an ethyl acetate/dichloromethane (30/70 by volume) mixture as eluent. 0.36 g of diethyl 1-(4-benzylcarbamoyl-1-oxoindan-2-yl)imidazole-2,4-dicarboxylate is thus obtained in the form of an oil which is used as is in the subsequent syntheses.

EXAMPLE 29

18 ml of 1N sodium hydroxide solution are added, under an argon blanket, to a stirred mixture, at a temperature in the region of 20° C., of 1.75 g of ethyl 8-(2-ethoxycarbonylethyl)-4,5-dihydro-4-oxo-10H-imidazo[1,2-a]indeno[1,2-e]pyrazin-2-carboxylate, 220 ml of dioxane and 60 ml of water and stirring is continued for 6 hours. The reaction mixture is filtered, the solid is washed with 2×20 ml of dioxane and 30 ml of water are added to the solid. The solution obtained is acidified to pH 1 with 1N hydrochloric acid and the precipitate is filtered, washed with 2×30 ml of distilled water and then 2×30 ml of acetone and dried under vacuum (1 mm Hg; 0.13 kPa) in the region of 50° C. 0.9 g of 8-(2-carboxyethyl)-4,5-dihydro-4-oxo-10H-imidazo[1,2-a]indeno[1,2-e]pyrazine-2-carboxylic acid is obtained in the form of a beige solid melting above 290° C. ($^1$H NMR spectrum in d6-DMSO, T=300 K, δ in ppm (200 MHz): 2.60 (2H, t, J=6 Hz, $CH_2CO_2H$), 2.90 (2H, t, J=6 Hz, $CH_2$), 4.00 (2H, s, $CH_2$), 7.25 (1H, d, J=8 Hz, arom. CH), 7.45 (1H, s, arom. CH), 7.78 (1H, d, J=8 Hz, arom. CH), 8.50 (1H, s, imidazole H), 12.5 (3H, s, NHCO and $2CO_2H$)).

Ethyl 8-(2-ethoxycarbonylethyl)-4,5-dihydro-4-oxo-10H-imidazo[1,2-a]indeno[1,2-e]pyrazine-2-carboxylate can be prepared in the following way: a mixture of 6.4 g of diethyl 1-[5-(2-ethoxycarbonylethyl)-1-oxoindan-2-yl]imidazole-2,4-dicarboxylate, 158 ml of acetic acid and 110 g of ammonium acetate is brought to reflux for 45 minutes. 160 ml of water are added to the reaction mixture and the precipitate obtained is filtered, washed with 2×20 ml of distilled water and then 2×20 ml of acetone and air-dried. The crude product (3 g) is crystallized from 300 ml of a mixture of dimethylformamide and distilled water (80/20 by volume) and the crystals are rinsed with 2×30 ml of distilled water and 2×30 ml of acetone. After drying under vacuum (1 mm Hg; 0.13 kPa) in the region of 50° C., 1.8 g of ethyl 8-(2-ethoxycarbonylethyl)-4,5-dihydro-4-oxo-10H-imidazo[1,2-a]indeno[1,2-e]pyrazine-2-carboxylate are obtained in the form of a light-grey solid melting above 290° C. ($^1$H NMR spectrum in d6-DMSO, T=300 K, δ in ppm (200 MHz): 1.20 (3H, t, J=6 Hz, $CH_3$), 1.37 (3H, t, J=6 Hz, $CH_3$), 2.68 (2H, t, J=6 Hz, $CH_2CO$), 2.90 (2H, t, J=6 Hz, $CH_2$), 4.00 (2H, s, $CH_2$), 4.05 (2H, q, J=6 Hz, $CH_2O$), 4.35 (2H, q, J=6 Hz, $CH_2O$), 7.25 (1H, d, J=8 Hz, arom. CH), 7.45 (1H, s, arom. CH), 7.78 (1H, d, J=8 Hz, arom. CH), 8.55 (1H, s, imidazole H), 12.5 (1H, s, NHCO)).

Diethyl 1-[5-(2-ethoxycarbonylethyl)-1-oxoindan-2-yl]imidazole-2,4-dicarboxylate can be prepared in the following way: a mixture of 4.6 g of diethyl imidazole-2,4-dicarboxylate, 94 ml of acetone and 15 g of potassium carbonate is brought to reflux under an inert atmosphere. A solution of 6.8 g of ethyl 3-(2-bromo-1-oxoindan-5-yl)propionate in 135 ml of acetone is then added dropwise and reflux is continued for 1 hour. The reaction mixture is filtered at a temperature in the region of 20° C. and the solid obtained is washed with 2×30 ml of acetone. The filtrate is evaporated on a rotary evaporator and the evaporation residue is chromatographed on a silica column, elution being carried out with a mixture of cyclohexane and ethyl acetate (75/25 by volume). 6.4 g of diethyl 1-[5-(2-ethoxycarbonylethyl)-1-oxoindan-2-yl]imidazole-2,4-dicarboxylate are obtained in the form of a light-orange solid melting at 106° C. ($^1$H NMR spectrum in d6-DMSO, T=300 K, δ in ppm (300 MHz): 1.15 (6H, t, J=6 Hz, $2CH_3$), 1.28 (3H, t, J=6 Hz, $CH_3$), 2.72 (2H, t, J=6 Hz, $CH_2CO$), 2.98 (2H, t, J=6 Hz, $CH_2$), 3.40 and 3.88 (each 1H, respectively dd, J=5 and 12 Hz, and dd, J=8 and 12 Hz, $CH_2$), between 3.90 and 4.30 (6H, m, $3CH_2O$), 5.85 (1H, dd, J=8 and 5 Hz, NCH), 7.42 (1H, d, J=8 Hz, arom. CH), 7.48 (1H, s, arom. CH), 7.65 (1H, d, J=8 Hz, arom. CH), 8.30 (1H, s, imidazole H)).

Ethyl 3-(2-bromo-1-oxoindan-5-yl)propionate can be prepared in the following way: a mixture of 5.8 g of ethyl 3-(1-oxoindan-5-yl)propionate, 100 ml of tetrahydrofuran and 9.4 g of phenyltrimethylammonium tribromide is stirred for 1 hour under an inert atmosphere at a temperature in the region of 20° C. The reaction mixture is treated with 250 ml of a 5 % aqueous sodium hydrogencarbonate solution and extracted with a total of 375 ml of ethyl acetate. The organic extract is dried over magnesium sulphate, filtered and evaporated on a rotary evaporator. The evaporation residue (10.6 g) is chromatographed on a silica column, elution being carried out with a mixture of cyclohexane and ethyl acetate (85/15 by volume). 7.3 g of ethyl 3-(2-bromo-1-oxoindan-5-yl)propionate are obtained in the form of a light-yellow oil ($^1$H NMR spectrum in d6-DMSO, T=300 K, $\delta$ in ppm (300 MHz): 1.15 (3H, t, J=6 Hz, CH$_3$), 2.70 (2H, t, J=6 Hz, CH$_2$CO), 3.00 (2H, t, J=6 Hz, CH$_2$), 3.35 and 3.87 (each 1H, respectively dd, J=2 and 12 Hz, and dd, J=6 and 12 Hz, CH$_2$), 4.05 (2H, q, J=6 Hz, CH$_2$O), 5.02 (1H, dd, J=6 and 2 Hz, CHBr), 7.40 (1H, d, J=8 Hz, arom. CH), 7.45 (1H, s, arom. CH), 7.67 (1H, d, J=8 Hz, arom. CH)).

Ethyl 3-(1-oxoindan-5-yl)propionate can be prepared in the following way: a mixture of 1.15 g of ethyl 3-(1-oxoindan-5-yl)acrylate, 23 ml of ethyl acetate and 0.11 g of 10 % palladium-on-charcoal is hydrogenated at a temperature in the region of 20° C. under a pressure of 2 bar for 3 hours. The reaction mixture is filtered under an inert atmosphere and the filtrate is evaporated on a rotary evaporator. The evaporation residue is chromatographed on a silica column, elution being carried out with a mixture of cyclohexane and ethyl acetate (87.5/12.5 by volume). 0.6 g of ethyl 3-(1-oxoindan-5-yl)propionate is obtained in the form of a very light-yellow solid melting at 53° C. ($^1$H NMR spectrum in d6-DMSO, T=300 K, $\delta$ in ppm (300 MHz): 1.12 (3H, t, J=6 Hz, CH$_3$), 2.57 (2H, t, J=6 Hz, CH$_2$CO), 2.65 (2H, t, J=6 Hz, CH$_2$), 2.98 (2H, t, J=6 Hz, CH$_2$CO), 3.05 (2H, t, J=6 Hz, CH$_2$), 4.05 (2H, q, J=6 Hz, CH$_2$O), 7.30 (1H, d, J=8 Hz, arom. CH), 7.42 (1H, s, arom. CH), 7.58 (1H, d, J=8 Hz, arom. CH)).

Ethyl 3-(1-oxoindan-5-yl)acrylate can be prepared in the following way: a mixture of 63 g of 5-bromoindan-1-one, 90 ml of tributylamine, 40.8 ml of ethyl acrylate, 3.65 g of tri-o-tolylphosphine and 0.67 g of palladium acetate is heated to a temperature in the region of 100° C. The heating bath is removed in the region of 105° C. and the temperature of the reaction mixture rapidly reaches 170° C. and then gradually falls. The mixture is maintained at a temperature in the region of 100° C. for 3 hours. 300 ml of 1N hydrochloric acid are added to the reaction mixture and extraction is carried out with a total of 750 ml of ethyl acetate. The organic phase is dried over magnesium sulphate, filtered and evaporated on a rotary evaporator. The evaporation residue (150 g) is chromatographed on a silica column, elution being carried out with a mixture of cyclohexane and dichloromethane (50/50 by volume). 49.5 g of ethyl 3-(1-oxoindan-5-yl)acrylate are obtained in the form of a yellow solid melting at 110° C. ($^1$H NMR spectrum in d6-DMSO, T=300 K, $\delta$ in ppm (300 MHz): 1.30 (3H, t, J=6 Hz, CH$_3$), 2.70 (2H, t, J=6 Hz, CH$_2$CO), 3.15 (2H, t, J=6 Hz, CH$_2$), 4.22 (2H, q, J=6 Hz, CH$_2$O), 6.80 (1H, d, J=16 Hz, ethylenic CH), 7.68 (1H, d, J=7 Hz, arom. CH), 7.75 (1H, d, J=16 Hz, ethylenic CH), 7.80 (1H, d, J=8 Hz, arom. CH), 7.95 (1H, s, arom. CH)).

5-Bromoindan-1-one can be synthesized as described by J. P. Quére and E. Maréchal, Bull. Soc. Chim. Fr., 8, 2983 (1971).

EXAMPLE 30

4.4 ml of 1N sodium hydroxide solution are added dropwise to a suspension of 0.56 g of ethyl 9-[(3-methylureido) methyl]-4,5-dihydro-4-oxo-10H-imidazo[1,2-a]indeno[1,2-e]pyrazin-2-carboxylate in a dioxane/water (4/1 by volume) mixture stirred at a temperature in the region of 20° C. The solution thus obtained is stirred for 5 hours at the same temperature. The reaction mixture is then concentrated to dryness under reduced pressure and the residue obtained taken up in 0.5N hydrochloric acid. The precipitate formed is filtered and then washed with ethyl ether and with acetone to result in 0.23 g of 9-[(3-methylureido)methyl]-4,5-dihydro-4-oxo-10H-imidazo[1,2-a]indeno[1,2-e]pyrazin-2-carboxylic acid in the form of a beige solid, the melting point of which is greater than 260° C. ($^1$H NMR spectrum in d6-DMSO, T=300 K, $\delta$ in ppm (250 MHz): 2.60 (3H, s, NCH$_3$), 4.05 (2H, s, CH$_2$), 4.35 (2H, s, NCH$_2$), 6.00 (1H, s, NH), 6.60 (1H, s, NH), 7.25 (1H, d, J=8 Hz, arom. CH), 7.40 (1H, t, J=8 Hz, arom. CH), 7.80 (1H, d, J=8 Hz, arom. CH), 8.55 (1H, s, imidazole H), 12.50 (1H, s, NHCO)).

Ethyl 9-[(3-methylureido)methyl]-4,5-dihydro-4-oxo-10H-imidazo[1,2-a]indeno[1,2-e]pyrazin-2-carboxylate can be prepared according to the following protocol: 0.58 ml of methyl isocyanate is added dropwise at a temperature in the region of 20° C. to a suspension of 0.8 g of ethyl 9-aminomethyl-4,5-dihydro-4-oxo-10H-imidazo[1,2-a]indeno[1,2-e]pyrazin-2-carboxylate in 60 ml of dimethylformamide. The reaction is continued overnight at the same temperature. The insoluble material is filtered and washed with dimethylformamide and then with ethyl ether. 0.56 g of the expected product is thus obtained in the form of a light-grey solid, the melting point of which is greater than 260° C. ($^1$H NMR spectrum in d6-DMSO+TFA, T=300 K, $\delta$ in ppm (300 MHz) (Very poorly resolved spectrum): 1.4 (3H, CH$_3$), 2.6 (3H, NCH$_3$), 4.1 (2H, CH$_2$), 4.4 (4H, NCH$_2$ and OCH$_2$), between 7.2 and 8.6 (4H, 3 arom. CH and 1 imidazole CH; EI Mass spectrum (70 ev) M/z: 381 (M$^+$·), 350, 336, 307, 278, 261, 57)).

Ethyl 9-aminomethyl-4,5-dihydro-4-oxo-10H-imidazo[1,2-a]indeno[1,2-e]pyrazin-2-carboxylate can be obtained according to the following procedure: 1.65 ml of hydrazine hydrate are added to 1.5 g of ethyl 9-phthalimidomethyl-4,5-dihydro-4-oxo-10H-imidazo[1,2-a]indeno[1,2-e]pyrazin-2-carboxylate in suspension in 80 ml of ethanol and the reaction mixture is brought to reflux for 24 hours. After cooling to a temperature in the region of 20° C., the insoluble material is filtered and then washed with ethanol and with ethyl ether. 1 g of the expected product is thus obtained in the form of a light-grey solid ($^1$H NMR spectrum in d6-DMSO, T=300 K, $\delta$ in ppm (400 MHz): 1.35 (3H, t, J=6 Hz, CH$_3$), 3.85 (2H, s, NCH$_2$), 4.05 (2H, s, CH$_2$), 4.38 (2H, q, J=6 Hz, CH$_2$O), between 7.40 and 8.10 (3H, m, 3 arom. CH), 8.60 (1H, s, imidazole H)).

Ethyl 9-phthalimidomethyl-4,5-dihydro-4-oxo-10H-imidazo[1,2-a]indeno[1,2-e]pyrazin-2-carboxylate can be prepared in the following way: the mixture consisting of 4.35 g of ethyl 1-(4-phthalimidomethyl-1-oxoindan-2-yl) imidazole-2,4-dicarboxylate, 40.9 g of ammonium acetate and 70 ml of acetic acid is brought to reflux for 7 hours. After cooling to a temperature in the region of 20° C., the insoluble material is filtered and washed with water and then with acetone to result in 2 g of the expected product in the form of a beige solid used without additional purification in the subsequent syntheses (EI Mass spectrum (70 ev) M/z: 454(M$^+$·), 408, 307, 261, 160)).

Ethyl 1-(4-phthalimidomethyl-1-oxoindan-2-yl) imidazole-2,4-dicarboxylate can be synthesized as follows: 15.2 g of 2-bromo-4-phthalimidomethylindan-1-one in 220 ml of acetone are added to a suspension of 6.27 g of ethyl imidazole-2,4-dicarboxylate and 20.4 g of potassium carbonate in 180 ml of acetone brought to reflux. The reaction is continued for 3 hours and 30 minutes at the same temperature. The reaction mixture is then cooled to a temperature in the region of 20° C. and the insoluble material filtered and then washed with acetone. The filtrate is concentrated to dryness under reduced pressure, then taken up in ethyl acetate and the insoluble material filtered. Ethyl 1-(4-phthalimidomethyl-1-oxoindan-2-yl)imidazole-2,4-dicarboxylate (3.6 g) is thus obtained in the form of a beige foam ($^1$H NMR spectrum in d6-DMSO, T=300 K, δ in ppm (250 MHz): 1.18 (3H, t, J=6 Hz, CH$_3$), 1.33 (3H, t, J=6 Hz, CH$_3$), 3.50 and 4.00 (each 1H, respectively dd, J=16 and 5 Hz, and dd, J=16 and 8 Hz, CH$_2$), 4.15 (2H, q, J=6 Hz, CH$_2$O), 4.30 (2H, q, J=6 Hz, CH$_2$O), 4.90 (2H, s, NCH$_2$), 5.91 (1H, dd, J=8 and 5 Hz, NCH), 7.53 (1H, t, J=8 Hz, arom. CH), 7.72 (2H, d, J=8 Hz, 2 arom. CH), between 7.80 and 8.00 (4H, m, phthalimide CH), 8.40 (1H, s, imidazole H)). 2-Bromo-4-phthalimidomethylindan-1-one can be prepared according to the following method: 2.64 ml of bromine, in solution in 50 ml of dichloromethane, are added dropwise, under nitrogen and at a temperature in the region of 0° C., over approximately 45 minutes to a suspension of 15 g of 4-phthalimidomethylindan-1-one in 100 ml of dichloromethane. The reaction is continued for 6 hours at a temperature in the region of 20° C. After addition of 100 ml of distilled water, the phases are separated by settling and the organic phase is washed with water, dried over magnesium sulphate, filtered and concentrated to dryness under reduced pressure to result in 17 g of the expected brominated compound in the form of a white solid melting at 173° C. ($^1$H NMR spectrum in d6-DMSO, T=300 K, δ in ppm (250 MHz): 3.50 and 4.05 (each 1H, respectively dd, J=16 and 2 Hz, and dd, J=16 and 8 Hz, CH$_2$), 4.90 (2H, s, NCH$_2$), 5.10 (1H, dd, J=8 and 2 Hz, BrCH), 7.50 (1H, t, J=8 Hz, arom. CH), 7.70 (2H, d, J=8 Hz, 2 arom. CH), between 7.80 and 8.00 (4H, m, phthalimide CH)).

4-Phthalimidomethylindan-1-one can be prepared in the following way: a solution of 3-[2-(phthalimidomethyl) phenyl]propionic acid chloride (prepared by reaction at 30° C. for 4 hours and 30 minutes of 83.39 g of 3-[2-(phthalimidomethyl)phenyl]propionic acid with 39.3 ml of thionyl chloride in 330 ml of dichloromethane) in 500 ml of 1,2-dichloroethane is added dropwise to 107.9 g of aluminium chloride in suspension in 800 ml of 1,2-dichloroethane at a temperature below 20° C. The reaction is continued overnight at 20° C. and the reaction mixture is then poured onto ice. The insoluble material thus formed is filtered and washed with a saturated aqueous sodium carbonate solution and then with distilled water. After drying, 41.1 g of 4-phthalimidomethylindan-1-one are obtained in the form of a white powder melting at 199° C. Extraction of the organic phase and concentration to dryness result in the recovery of an additional 30 g of the expected product ($^1$H NMR spectrum in d6-DMSO, T=300 K, δ in ppm (250 MHz): 2.70 (2H, t, J=6 Hz, CH$_2$CO), 3.20 (2H, t, J=6 Hz, CH$_2$), 4.90 (2H, s, NCH$_2$), 7.40 (1H, t, J=8 Hz, arom. CH), 7.60 (2H, d, J=8 Hz, 2 arom. CH), between 7.80 and 8.00 (4H, m, phthalimide CH)).

3-[2-(Phthalimidomethyl)phenyl]propionic acid can be obtained according to the following procedure: 4 g of 10% palladium-on-charcoal are added to a solution of 95 g of o-(phthalimidomethyl)cinnamic acid in 900 ml of dimethylformamide and the mixture is placed under hydrogen at a pressure in the region of 1 bar and at a temperature in the region of 20° C. After reacting for 15 hours, the reaction mixture is filtered on celite, the insoluble material is washed with dimethylformamide and the filtrate is concentrated to dryness under reduced pressure. The residue is taken up in ethyl ether and the insoluble material is filtered and dried to result in 88.39 g of the expected product in the form of a white powder melting at 180° C. ($^1$H NMR spectrum in d6-DMSO, T=300 K, δ in ppm (200 MHz): 2.60 (2H, t, J=6 Hz, CH$_2$CO), 3.02 (2H, t, J=6 Hz, CH$_2$), 4.83 (2H, s, NCH$_2$), between 7.00 and 7.40 (4H, m, 4 arom. CH), between 7.80 and 8.00 (4H, m, phthalimide CH), 12.20 (1H, s, COOH)).

o-(Phthalimidomethyl)cinnamic acid can be obtained according to the following method: 149 g of 1-bromo-2-phthalimidomethylbenzene, 337 ml of tributylamine, 5.7 g of tri-o-tolylphosphine, 1 g of palladium acetate and 40 ml of acrylic acid are successively introduced into a round-bottomed flask under a stream of nitrogen. The suspension is heated for 2 hours at 100° C. and then left overnight at a temperature in the region of 20° C. A black oily phase is separated by settling and then run onto an aqueous hydrochloric acid solution (170 ml of 12N hydrochloric acid in 1 l of distilled water). The precipitate formed is filtered, washed with water and dried. The greyish powder obtained is taken up in dimethylformamide (500 ml) at 60° C. and treated with animal charcoal. Filtration on celite and concentration to dryness of the filtrate result in a yellow paste which is taken up in ethyl ether and then the insoluble material is filtered and dried. 95.8 g of the expected cinnamic acid are obtained in the form of a white powder melting at 234° C. (EI Mass spectrum (70 eV) M/z: 307 (M$^{+\cdot}$), 261, 160, 147, 115).

1-Bromo-2-phthalimidomethylbenzene can be obtained as follows: a solution of 150 g of o-bromobenzyl bromide in 1.2 liters of dimethylformamide is treated with 155.5 g of potassium phthalimide and heated at 60° C. for 5 hours. After cooling to a temperature in the region of 20° C., the reaction mixture is filtered and the insoluble material washed with methanol and dried. 59 g of the expected product are thus obtained in the form of a white powder melting at 170° C. The filtrate is concentrated to dryness under reduced pressure and the residue taken up in 200 ml of methanol; the insoluble material is filtered, washed with methanol and dried to result in an additional 88.2 g of the expected product in the form of a white powder melting at 165° C. ($^1$H NMR spectrum in d6-DMSO, T=300 K, δ in ppm (200 MHz): 4.80 (2H, s, NCH$_2$) between 7.10 and 7.40 (3H, m, 3 arom. CH), 7.65 (1H, d, J=8 Hz, arom. CH), between 7.80 and 8.10 (4H, m, phthalimide CH)).

EXAMPLE 31

A solution of 0.4 g of diethyl 9-ethoxycarbonylmethyl-4,5-dihydro-4-oxo-10H-imidazo[1,2 a]indeno[1,2-e]pyrazin-2-phosphonate in 10 ml of 6N hydrochloric acid is heated at 100° C. for 24 hours. The insoluble material formed is filtered and washed with water and then with acetone to result, after drying, in 0.18 g of the hydrochloride of 9-carboxymcarboxymethyl-4,5-dihydro-4-oxo-10H-imidazo[1,2-a]indeno[1,2-e]pyrazin-2-phosphonic acid in the form of a white powder, the melting point of which is greater than 260° C. (Analysis C$_{15}$H$_{12}$N$_3$O$_6$P.HCl; % Calculated C: 45.30, H: 3.29, N: 10.57, P: 7.79; % Found C: 45.6, H: 3.7, N: 10.5, P: 7.5; $^1$H NMR spectrum in d6-DMSO, T=300 K, δ in ppm (300 MHz): 3.75 (2H, s, COCH$_2$), 4.00 (2H, s, CH$_2$), 7.25 (1H, d, J=8 Hz, arom. CH), 7.40 (1H, t, J=8 Hz, arom. CH), 7.80 (1H, d, J=8 Hz, arom. CH), 8.22 (1H, s, imidazole H), 12.50 (1H, s, NHCO)).

Diethyl 9-ethoxycarbonylmethyl-4,5-dihydro-4-oxo-10H-imidazo[1,2-a]indeno[1,2-e]pyrazin-2-phosphonate can be prepared according to the following protocol: the mixture consisting of 0.995 g of diethyl 2-ethoxycarbonyl-1-(4-ethoxycarbonylmethyl-1-oxoindan-2-yl)imidazole-4-phosphonate, 7 g of ammonium acetate and 20 ml of acetic acid is brought to reflux for 4 hours. After cooling to a temperature in the region of 20° C., the reaction mixture is poured into a mixture of water and crushed ice and the organic phase is extracted with ethyl acetate, washed with water, dried over sodium sulphate, filtered and concentrated to dryness under reduced pressure. The brown oil thus obtained is purified by medium-pressure silica chromatography, a mixture of dichloromethane and methanol (98/2 by volume) being used as eluent. 0.4 g of the expected product is isolated in the form of a greyish crystalline powder ($^1$H NMR spectrum in d6-DMSO, T=300 K, δ in ppm (300 MHz): between 1.10 and 1.40 (9H, m, 3 CH$_3$), 3.80 (2H, s, COCH$_2$), 4.00 (2H, s, CH$_2$) between 4.05 and 4.20 (6H, m, 3 CH$_2$O), 7.22 (1H, d, J=8 Hz, arom. CH), 7.40 (1H, t, J=8 Hz, arom. CH), 7.80 (1H, d, J=8 Hz, arom. CH), 8.45 (1H, s, imidazole H), 12.50 (1H, s, NHCO)).

Diethyl 2-ethoxycarbonyl-1-(4-ethoxycarbonylmethyl-1-oxoindan-2-yl)imidazole-4-phosphonate can be obtained as follows: 3.15 g of ethyl (2-bromo-1-oxoindan-4-yl)acetate in 20 ml of acetone are added to a suspension of 2.1 g of diethyl 2-(ethoxycarbonyl)imidazole-4-phosphonate and 7 g of potassium carbonate in 45 ml of acetone brought to reflux. The reaction is continued for 2 hours at the same temperature. The reaction mixture is then cooled to a temperature in the region of 20° C. and the insoluble material filtered and then washed with acetone. The filtrate is concentrated to dryness under reduced pressure and the black residue purified by flash chromatography on silica, using ethyl acetate as eluent. The expected product (0.995 g) is thus obtained in the form of a yellow oil ($^1$H NMR spectrum in d6-DMSO, T=300 K, δ in ppm (300 MHz): between 1.00 and 1.40 (12H, m, 4 CH$_3$), 3.35 and 3.95 (each 1H, respectively dd, J=16 and 5 Hz, and dd, J=16 and 8 Hz, CH$_2$), 3.85 (2H, s, COCH$_2$), between 4.00 and 4.20 (8H, m, 4 CH$_2$O), 5.90 (1H, dd, J=8 and 5 Hz, NCH), 7.51 (1H, t, J=8 Hz, arom. CH), 7.70 (2H, d, J=8 Hz, 2 arom. CH), 8.25 (1H, s, imidazole H)).

Diethyl 2-(ethoxycarbonyl)imidazole-4-phosphonate can be prepared in the following way: a solution of 1.2 g of ethyl (hydroxyamino)iminoacetate in 20 ml of chloroform and 1.4 ml of triethylamine is cooled to a temperature in the region of 10° C. and a solution of 1.54 g of diethyl ethynylphosphonate in 5 ml of chloroform is added dropwise. The reaction mixture is stirred overnight at a temperature in the region of 20° C., 0.15 g of diethyl ethynylphosphonate is added and the reaction mixture is heated for 1 hour at a temperature in the region of 50° C. 50 ml of dichloromethane are added to the reaction mixture and the reaction mixture is washed with 3×40 ml of saturated sodium chloride solution. The organic phase is evaporated on a rotary evaporator, 40 ml of ethyl ether are added to the evaporation residue and filtration is carried out. The filtrate is evaporated on a rotary evaporator to give a yellow oil (2.4 g). 20 ml of xylene are added to this oil and heating is carried out at reflux for 20 hours. The liquid phase is separated by settling and evaporated on a rotary evaporator. The evaporation residue is purified by chromatography on a silica column, elution being carried out with ethyl acetate. 0.5 g diethyl 2-(ethoxycarbonyl)imidazole-4-phosphonate is obtained in the form of a yellow oil (Mass spectrum (electron impact) m/z 276 (M)$^{+\cdot}$, 247 (276-C$_2$H$_5$)$^+$, 231 (276-C$_2$H$_5$O)$^+$, 204 (C$_6$H$_9$N$_2$O$_4$P)$^{+\cdot}$, 157 (C$_4$H$_2$N$_2$O$_3$P)$^+$).

Ethyl (hydroxyamino)iminoacetate can be synthesized as described by W. K. Warburton, J. Chem. Soc. (C), 1522 (1966).

Diethyl ethynylphosphonate can be synthesized as described by D. T. Monaghan et al., Brain Res., 278, 138 (1983).

EXAMPLE 32

8.2 ml of 1N sodium hydroxide solution are added dropwise, under a stream of nitrogen and at a temperature in the region of 20° C., to a suspension of 1 g of ethyl 9-(N-methylaminocarbonylmethyl)-4,5-dihydro-4-oxo-10H-imidazo[1,2-a]indeno[1,2-e]pyrazin-2-carboxylate in a dioxane distilled water (100/27 by volume) mixture. The reaction is continued for 2 hours at the same temperature. The light-grey insoluble material is filtered, washed with acetone and then taken up in 15 ml of distilled water. This aqueous solution is filtered and then acidified to pH 1 with N hydrochloric acid. The precipitate formed is filtered and washed with water, with acetone and then with ethyl ether to result in 0.59 g of the trihydrate of 9-(N-methylaminocarbonylmethyl)-4,5-dihydro-4-oxo-10H-imidazo[1,2-a]indeno[1,2-e]pyrazin-2-carboxylic acid in the form of a white powder, the melting point of which is greater than 260° C. (Analysis C17H14N4O4.3H$_2$O; % Calculated C: 60.35, H: 4.17, N: 16.56; % Found C: 60.0, H: 4.1, N: 16.3; $^1$H NMR spectrum in CD$_3$CO$_2$D, T=300 K, δ in ppm (300 MHz): 2.7 (3H, s, NCH$_3$), 3.9 (2H, , CH$_2$CO), 4.1 (2H, s, CH$_2$), 7.2 (1H, d, J=8 Hz, arom. CH), 7.4 (1H, t, J=8 Hz, arom. CH), 7.7 (1H, d, J=8 Hz, arom. CH), 8.5 (1H, s, imidazole H)).

Ethyl 9-(N-methylaminocarbonylmethyl)-4,5-dihydro-4-oxo-10H-imidazo[1,2-a]indeno[1,2-e]pyrazin-2-carboxylate can be prepared according to the following protocol: the mixture consisting of 1.5 g of ethyl 1-[4-(N-methylaminocarbonylmethyl)-1-oxoindan-2-yl]imidazole-2,4-dicarboxylate, 14.2 g of ammonium acetate and 60 ml of acetic acid is brought to reflux for 6 hours. After cooling to a temperature in the region of 20° C., the insoluble material is filtered and washed with water and then with acetone. 1 g of the expected product is thus isolated in the form of a greyish solid, the melting point of which is greater than 260° C. ($^1$H NMR spectrum in d6-DMSO, T=300 K, δ in ppm (300 MHz): 1.35 (3H, t, J=6 Hz, CH$_3$), 2.60 (3H, d, J=5 Hz, NCH$_3$), 3.60 (2H, q, CH$_2$CO), 4.05 (2H, s, CH$_2$), 4.35 (2H, q, J=6 Hz, CH$_2$O), 7.20 (1H, d, J=8 Hz, arom. CH), 7.40 (1H, t, J=8 Hz, arom. CH), 7.75 (1H, d, J=8 Hz, arom. CH), 8.60 (1H, s, imidazole H)).

Ethyl 1-[4-(N-methylaminocarbonylmethyl)-1-oxoindan-2-yl]imidazole-2,4-dicarboxylate can be obtained as follows: a solution of 3.77 g of ethyl imidazole-2,4-dicarboxylate, 6.14 g potassium carbonate and 0.117 g of crown ether 18-c-6 in 225 ml of dimethylformamide is heated for 2 hours at 85° C. under a stream of nitrogen. After cooling to a temperature in the region of 20° C., a solution of 5 g of N-methyl-(2-bromo-1-oxoindan-4-yl)acetamide in 75 ml of dimethylformamide is added dropwise to the reaction mixture. The reaction is continued overnight at the same temperature. The reaction mixture is concentrated to dryness under reduced pressure, the residue is then taken up in distilled water and the organic phase extracted with dichloromethane, washed with water, dried over magnesium sulphate, treated with 3S charcoal, filtered and concentrated to dryness under reduced pressure. The brown oil thus obtained is taken up in acetonitrile and the precipitate formed is filtered and dried. The expected product (1.5 g) is obtained in the form of a white solid which decomposes at 166° C. ($^1$H NMR spectrum in d6-DMSO, T=300 K, δ in ppm (300 MHz): 1.12 (3H, t, J=6 Hz, CH$_3$), 1.30 (3H, t, J=6 Hz, CH$_3$), 2.60 (3H, d, J=5 Hz, NCH$_3$), 3.33 and 3.81 (each 1H, respectively dd, J=16 and 5 Hz, and dd, J=16 and 8 Hz, CH$_2$), 3.55 (2H, s, COCH$_2$), 4.12 (2H, q, J=6 Hz, CH$_2$O), ), 4.30 (2H, q, J=6 Hz, CH$_2$O), 5.90 (1H, dd, J=8 and 5 Hz, NCH), 7.51 (1H, t, J=8 Hz, arom. CH), between 7.60 and 7.75 (2H, m, 2 arom. CH), 8.05 (1H, q, J=5 Hz, NH), 8.32 (1H, s, imidazole H)).

N-Methyl-(2-bromo-1-oxoindan-4-yl)acetamide can be prepared according to the following procedure: 1.05 ml of bromine, in solution in 25 ml of dichloromethane, are added dropwise over approximately 30 minutes, under nitrogen and at a temperature in the region of 0° C., to a solution of 4.18 g of N-methyl-(1-oxoindan-4-yl)acetamide in a mixture of dichloromethane (100 ml) and ethanol (150 ml). The reaction is continued for 5 hours at a temperature in the region of 20° C. The reaction mixture is then concentrated to dryness under reduced pressure and the residue obtained is then taken up in dichloromethane. The insoluble material is filtered, washed with ethyl acetate and dried. 5 g of the expected brominated compound are obtained in the form of a yellow solid used without additional purification in the subsequent stages ($^1$H NMR spectrum in d6-DMSO, T=300 K, δ in ppm (300 MHz): 2.60 (3H, d, J=5 Hz, NCH$_3$), 3.32 and 3.88 (each 1H, respectively dd, J=16 and 2 Hz, and dd, J=16 and 8 Hz, CH$_2$), 3.50 (2H, s, COCH$_2$), 5.05 ($^1$H, dd, J=8 and 2 Hz, BrCH), between 7.35 and 7.70 (3H, m, 3 arom. CH), 8.00 (1H, s, NHCO)).

N-Methyl-(l-oxoindan-4-yl)acetamide can be synthesized as follows: a solution of 4.5 g of (1-oxoindan-4-yl)acetic acid in 100 ml of tetrahydrofuran is treated under a nitrogen atmosphere and at 0° C. with 5.7 g of N,N'-carbonyldiimidazole. The reaction is continued for 1 hour and 30 minutes at a temperature in the region of 20° C. After cooling to −5° C., 2.67 g of methylamine hydrochloride are added to the reaction mixture and stirring is continued overnight at a temperature in the region of 20° C. The concentration under reduced pressure of the reaction mixture results in a residue which is taken up in dichloromethane and this organic phase is washed with water, dried over magnesium sulphate, filtered and concentrated to dryness under reduced pressure. 3.9 g of the expected amide are thus obtained in the form of a yellow oil which crystallizes (EI Mass spectrum (70 ev) M/z: 203(M$^+$), 146, 117, 58)).

EXAMPLE 33

19 ml of 1N sodium hydroxide solution are added dropwise, under a stream of nitrogen and at a temperature in the region of 20° C., to a suspension of 1.9 g of ethyl 9-(1-ethoxycarbonylethyl)-4,5-dihydro-4-oxo-10H-imidazo[1,2-a]indeno[1,2-e]pyrazin-2-carboxylate in a mixture of dioxane (245 ml) and distilled water (65 ml). The reaction is continued for 4 hours and 30 minutes at the same temperature. The insoluble material, formed after partial evaporation of the solvents, is filtered, washed with water and then with a mixture of dimethylformamide (10 ml) and methanol (80 ml), and dried. The solid is dissolved in 20 ml of 1N sodium hydroxide solution and stirred for 4 hours at a temperature in the region of 20° C. The reaction mixture is then treated with 1N hydrochloric acid to pH 1 and the precipitate formed is filtered, washed with water and then with acetone and dried to result in 0.62 g of the hydrate of 9-(1-carboxyethyl)-4,5-dihydro-4-oxo-10H-imidazo[1,2-a]indeno[1,2-e]pyrazin-2-carboxylic acid in the form of a pink powder, the melting point of which is greater than 260° C. (Analysis C17H13N3O5.1.4H2O; % Calculated C: 60.18, H: 3.86, N: 12.38; % Found C: 60.1, H: 3.2, N: 12.5; $^1$H NMR spectrum in d6-DMSO, T=300 K, δ in ppm (300 MHz): 1.5 (3H, CH$_3$), 3.9 (1H, CH), 4.1 (2H, CH$_2$), 7.3, 7.5, 7.9 (each 1H, 3 arom. CH), 8.6 (1H, imidazole CH), between 12 and 13.5 (3H, 2 COOH and NHCO)).

Ethyl 9-(1-ethoxycarbonylethyl)-4,5-dihydro-4 -oxo-10H-imidazo[1,2-a]indeno[1,2-e]pyrazin-2-carboxylate can be obtained as follows: the mixture consisting of 3.67 g of ethyl 1-[4-(1-ethoxycarbonylethyl)-1-oxoindan-2-yl] imidazole-2,4-5 dicarboxylate, 40 g of ammonium acetate and 80 ml of acetic acid is brought to reflux for 3 hours. After cooling to a temperature in the region of 20° C., the insoluble material is filtered and washed with water. 1.9 g of the expected product are thus isolated in the form of a pink powder, the melting point of which is greater than 260° C., which is used without additional purification in the subsequent syntheses.

Ethyl 1-[4-(1-ethoxycarbonylethyl)-1-oxoindan-2-yl] imidazole-2,4-dicarboxylate can be prepared according to the following procedure: a solution of 5.24 g of ethyl imidazole-2,4-dicarboxylate and 16 g of potassium carbonate in 100 ml of acetone is heated at reflux under a stream of nitrogen. A solution of 7.7 g of ethyl 2-(2-bromo-1-oxoindan-4-yl)propionate in 50 ml of acetone is then added dropwise and reflux is continued for 3 hours. After cooling to a temperature in the region of 20° C., the insoluble material is filtered and washed with acetone and the filtrate is concentrated to dryness under reduced pressure. The crude product obtained is purified by flash chromatography on a silica column, using dichloromethane and then a dichloromethane/methanol (98/2 by volume) mixture as eluents. A second flash chromatographic operation on a silica column, using a mixture of ethyl acetate and cyclohexane (60/40 by volume) as eluent, results in 3.67 g of the expected product in the form of an orange-coloured oil.

Ethyl 2-(2-bromo-1-oxoindan-4-yl)propionate can be prepared in the following way: 1.2 ml of bromine, in solution in 10 ml of dichloromethane, are added dropwise, under nitrogen and at a temperature in the region of 15° C., to a solution of 5.64 g of ethyl α-methyl-(1-oxoindan-4-yl) acetate in 50 ml of dichloromethane. The reaction is continued for 2 hours at a temperature in the region of 20° C. 40 ml of distilled water are then added to the reaction mixture and the organic phase is separated, washed with water, dried and concentrated to dryness under reduced pressure. 7.7 g of the expected brominated compound are obtained in the form of a rust-coloured oil used without additional purification in the subsequent stages.

Ethyl α-methyl-(1-oxoindan-4-yl)acetate can be synthesized according to the following protocol: 4 ml of oxalyl chloride are added dropwise to 8.6 g of α-methyl-(1-oxoindan-4-yl)acetic acid in solution in a mixture of 140 ml of dichloromethane and 32 ml of absolute ethanol, the temperature being maintained below 25° C. After stirring for 4 hours at a temperature in the region of 20° C., the reaction mixture is concentrated to dryness under reduced pressure and the residue taken up in distilled water and dichloromethane. The organic phase is separated, washed with water, dried and concentrated to dryness under reduced pressure. The brown oil obtained is purified by flash chromatography on a silica column, dichloromethane being used as eluent. 5.64 g of the expected ester are thus obtained in the form of a rust-coloured oil.

α-Methyl-(1-oxoindan-4-yl)acetic acid can be obtained according to the following method: 50 g of phosphorus pentoxide are added to 40 g of phosphoric acid and the mixture is heated at 130° C. for 3 hours. The mixture is then cooled to 90° C., at which temperature 10.4 g of 3-[o-(1-carboxyethyl)phenyl]propionic acid are introduced. The reaction is continued for 30 minutes at 90° C. After cooling to a temperature in the region of 20° C., the reaction mixture is poured onto crushed ice. The organic phase is extracted with ethyl acetate, washed with water, dried over sodium sulphate, filtered and concentrated to dryness under reduced pressure. 8.6 g of the expected indanone are thus obtained in the form of a yellow foam ($^1$H NMR spectrum in d6-DMSO, T=300 K, δ in ppm (300 MHz): 1.42 (3H, d, J=5 Hz, NCH$_3$), 2.70 (2H, m, COCH$_2$), 3.12 (2H, t, J=6 Hz, CH$_2$), 3.97 (1H, q, J=6 Hz, CH), between 7.40 and 7.75 (3H, m, 3 arom. CH)).

3-[o-(1-Carboxyethyl)phenyl]propionic acid can be prepared as follows: 13 g of o-(1-carboxyethyl)cinnamic acid, in solution in 130 ml of dimethylformamide, are hydrogenated in the presence of 0.9 g of 10% palladium-on-charcoal at a temperature in the region of 20° C. under a pressure of 1.2 bar for 3 hours. After filtering the reaction mixture on celite and washing the insoluble material with dimethylformamide, the filtrate is concentrated to dryness under reduced pressure. The expected propionic acid is thus obtained (10.4 g) in the form of a pale-yellow powder melting at 154° C. ($^1$H NMR spectrum in d6-DMSO, T=300 K, δ in ppm (200 MHz): 1.30 (3H, d, J=6 Hz, CH$_3$), 2.50 (2H, m, COCH$_2$), 2.90 (2H, m, CH$_2$), 3.90 (1H, q, J=6 Hz, CH), between 7.10 and 7.40 (4H, m, 4 arom. CH), 12.30 (2H, s, 2COOH)).

o-(1-Carboxyethyl)cinnamic acid can be synthesized in the following way: 23.34 g of 2-(o-bromophenyl)propionic acid, 400 ml of distilled water, 185 ml of a 1.6M aqueous sodium carbonate solution, 2.24 g of palladium acetate and 10.35 ml of acrylic acid are successively introduced into a round-bottomed flask under a stream of nitrogen. The suspension is heated for 17 hours at reflux. 5 ml of acrylic acid and 1 g of palladium acetate are then again added and the reaction mixture is again heated at reflux for 18 hours. After cooling to a temperature in the region of 20° C., the reaction mixture is filtered, washed with water and then acidified using 6N hydrochloric acid. The precipitate formed is filtered, washed with water and then with dichloromethane and dried. 13 g of the expected cinnamic acid are obtained in the form of a brown powder melting at 176° C. ($^1$H NMR spectrum in d6-DMSO, T=300 K, δ in ppm (300 MHz): 1.35 (3H, d, J=6 Hz, CH$_3$), 4.08 (1H, q, J=6 Hz, CH), 6.48 (1H, d, J=16 Hz, ethylenic CH), between 7.30 and 7.55 (3H, m, 3 arom. CH), 7.75 (1H, d, J=8 Hz, arom. CH), 8.00 (1H, d, J=16 Hz, ethylenic CH), 12.50 (2H, s, 2 COOH)).

2-(o-Bromophenyl)propionic acid can be prepared as follows: 17 g of methyl 2-(o-bromophenyl)propionate are stirred with 100 ml of N sodium hydroxide solution in 100 ml of tetrahydrofuran at a temperature in the region of 20° C. for 4 hours. The reaction mixture is then acidified using N hydrochloric acid and the organic phase is extracted with dichloromethane, washed with water, dried and concentrated to dryness under reduced pressure to result in 16.4 g of the expected acid in the form of a foam used without additional purification in the subsequent syntheses.

Methyl 2-(o-bromophenyl)propionate can be prepared according to the following procedure: 54 g of dimethyl sulphate are added, at a temperature in the region of 20° C., to a solution of 15 g of o-bromophenylacetic acid in 150 ml of dichloromethane. 37 g of crushed potassium hydroxide and then 4.98 g of triethylbenzylammonium chloride are added to this solution, which has been cooled to 5° C. The reaction is continued overnight at a temperature in the region of 20° C. The reaction mixture is then poured into 100 ml of water and the organic phase is separated by settling, washed with N hydrochloric acid and then with water, dried and concentrated to dryness under reduced pressure. 17 g of the expected product are thus obtained in the form of a yellow oil ($^1$H NMR spectrum in d6-DMSO, T=300 K, δ in ppm (250 MHz) 1.45 (3H, d, J=6 Hz, CH$_3$), 3.65 (3H, s, OCH$_3$), 4.20 (1H, q, J=6 Hz, CH), between 7.20 and 7.50 (3H, m, 3 arom. CH), 7.67 (1H, d, J=8 Hz, arom. CH)).

The medicaments according to the invention consist of a compound of formula (I) or a salt of such a compound, in the pure state or in the form of a composition in which it is combined with any other pharmaceutically compatible product, which can be inert or physiologically active. The medicaments according to the invention can be used orally, parenterally, rectally or topically.

Tablets, pills, powders (gelatin capsules or cachets) or granules can be used as solid compositions for oral administration. In these compositions, the active principle according to the invention is mixed with one or a number of inert diluents, such as starch, cellulose, sucrose, lactose or silica, under a stream of argon. These compositions can also comprise substances other than the diluents, for example one or a number of lubricating agents such as magnesium stearate or talc, a colouring agent, a coating (dragées) or a varnish.

Pharmaceutically acceptable solutions, suspensions, emulsions, syrups and elixirs containing inert diluents such as water, ethanol, glycerol, vegetable oils or paraffin oil can be used as liquid compositions for oral administration. These compositions can comprise substances other than the diluents, for example wetting, sweetening, thickening, flavouring or stabilizing substances.

The sterile compositions for parenteral administration can preferably be suspensions, emulsions or aqueous or non-aqueous solutions. Water, propylene glycol, a polyethylene glycol, vegetable oils, in particular olive oil, injectable organic esters, for example ethyl oleate, or other suitable organic solvents can be used as solvent or vehicle. These compositions can also contain adjuvants, in particular wetting, isotonizing, emulsifying, dispersing and stabilizing agents. Sterilization can be carried out in several ways, for example by aseptic filtration, by incorporating sterilizing agents in the composition, by irradiation or by heating. They can also be prepared in the form of sterile solid compositions which can be dissolved at the time of use in sterile water or any other injectable sterile medium.

The compositions for rectal administration are suppositories or rectal capsules which contain, besides the active product, excipients such as cocoa butter, semi-synthetic glycerides or poly(ethylene glycol) s.

The compositions for topical administration can be, for example, creams, lotions, eye drops, mouth washes, nose drops or aerosols.

In human therapeutics, the compounds according to the invention are particularly useful for the treatment and/or the prevention of conditions which require the administration of an antagonist of the AMPA receptor or of an antagonist of the NMDA receptor. These compounds are especially useful for treating or preventing all ischaemias and in particular cerebral ischaemia, the effects due to anoxia, the development of neurodegenerative diseases, Huntington's chorea, Alzheimer's disease, and other dementias, amyotrophic lateral sclerosis or other motoneuron diseases, olivopontocerebellar atrophy, Parkinson's disease, with respect to epileptogenic and/or convulsive symptoms, cerebral or spinal traumas, traumas related to degeneration of the inner ear or of the retina, tinnitus, anxiety, depression, schizophrenia, Tourette's syndrome, hepatic encephalopathies, sleep disorders, attention deficit disorders or disorders of hormonal conditions (excess secretion of HG or HL or secretion of corticosterone), as analgesics, antiinflammatories, antianorexics, antimigraines and antiemetics, and for treating poisonings by neurotoxins or other agonist substances of the NMDA or AMPA receptor, and neurological disorders associated with viral diseases such as viral meningitides and encephalitides, AIDS, rabies, measles and tetanus, for preventing, tolerating and depending on symptoms of withdrawal from drugs or from alcohol and inhibiting addiction to and dependence on opiates, barbiturates, amphetamine and benzodiazepines, and in the treatment of deficiencies related to mitochondrial anomalies such as mitochondrial myopathy, Leber's syndrome, Wernicke's encephalopathy, Rett's syndrome, homocysteinaemia, hyperprolinaemia, hydroxybutiricaminoaciduria, saturnine encephalopathy (chronic lead poisoning) and sulphite oxidase deficiency.

The doses depend on the desired effect, on the duration of treatment and on the administration route used; they are generally between 10 mg and 100 mg per day orally for an adult with unit doses ranging from 5 mg to 50 mg of active substance.

Generally, the doctor will determine the appropriate dosage depending on the age, weight and all the other factors specific to the subject to be treated.

The following examples illustrate compositions according to the invention:

Example A

Gelatin capsules containing 50 mg of active product are prepared, according to the usual technique, which have the following composition:

| | | |
|---|---|---|
| Compound of formula (I) | 50 mg | |
| Cellulose | 18 mg | |
| Lactose | 55 mg | |
| Colloidal silica | 1 mg | |
| Sodium carboxymethylstarch | 10 mg | |
| Talc | 10 mg | |
| Magesium stearate | 1 mg | |

Example B

Tablets containing 50 mg of active product are prepared, according to the usual technique, which have the following composition:

| | | |
|---|---|---|
| Compound of formula (I) | 50 mg | |
| Lactose | 104 mg | |
| Cellulose | 40 mg | |
| Polyvidone | 10 mg | |
| Sodium carboxymethylstarch | 22 mg | |
| Talc | 10 mg | |
| Magnesium stearate | 2 mg | |
| Colloidal silica | 2 mg | |
| Mixture of hydroxymethylcellulose; glycerol and titanium oxide (72/3.5/24.5) q.s. 1 coated tablet completed to | 245 mg | |

Example C

An injectable solution containing 10 mg of active product is prepared which has the following composition:

| | | |
|---|---|---|
| Compound of formula (I) | 10 mg | |
| Benzoic acid | 80 mg | |
| Benzyl alcohol | 0.06 ml | |
| Sodium benzoate | 80 mg | |
| 95% ethanol | 0.4 ml | |
| Sodium hydroxide | 24 mg | |
| Propylene glycol | 1.6 ml | |
| Water q.s. | 4 ml | |

What is claimed is:

1. A compound of formula (II):

(II)

[chemical structure showing an indanone fused to an imidazole ring with substituent R on imidazole, COOalk group, and R$_1$ on the benzene ring]

in which

R represents a hydrogen atom or a carboxy, alkoxycarbonyl, —CO—NR$_4$R$_5$, —PO$_3$H$_2$ or —CH$_2$OH radical, R$_1$ represents an -alk-NH$_2$, -alk-NH—CO—R$_3$, -alk-COOR$_4$, -alk-CO—NR$_5$R$_6$ or —CO—NH—R$_7$ radical, R$_3$ represents an alkyl, phenyl, phenylalkyl, cycloalkyl or —NR$_6$R$_8$ radical, R$_4$ represents a hydrogen atom or an alkyl radical, R$_5$ represents a hydrogen atom or an alkyl, phenyl, cycloalkyl or phenylalkyl radical, R$_6$ represents a hydrogen atom or an alkyl radical, or, alternatively, R$_5$ and R$_6$ form, with the nitrogen atom to which they are attached, a saturated or unsaturated, mono- or polycyclic heterocycle containing 1 to 6 carbon atoms and optionally at least one other heteroatom selected from O, S and N, R$_7$ represents a phenyl, phenylalkyl or -alk-COOR$_4$ radical, R$_8$ represents a hydrogen atom or an alkyl, cycloalkyl or phenylalkyl radical, and alk represents an alkyl radical containing 1 to 6 carbon atoms in a straight or branched chain;

with the proviso that the alkoxy, alkyl and alkylene radicals and portions of radicals contain 1 to 6 carbon atoms and are in a straight or branched chain and that the cycloalkyl radicals contain 3 to 6 carbon atoms;

a salt thereof, an enantiomer thereof, or a diastereoisomer thereof.

* * * * *